(12) United States Patent
D'Onofrio et al.

(10) Patent No.: US 8,334,281 B2
(45) Date of Patent: Dec. 18, 2012

(54) NASAL FORMULATIONS OF METOCLOPRAMIDE

(75) Inventors: Matthew J. D'Onofrio, San Diego, CA (US); David A. Gonyer, Cardiff, CA (US); Shirish A. Shah, Phoenix, AZ (US); Stuart J. Madden, Ellicott City, MD (US)

(73) Assignee: Evoke Pharma, Inc., San Diego, CA (US)

( * ) Notice: Subject to any disclaimer, the term of this patent is extended or adjusted under 35 U.S.C. 154(b) by 145 days.

(21) Appl. No.: 12/645,108

(22) Filed: Dec. 22, 2009

(65) Prior Publication Data
US 2010/0163032 A1 Jul. 1, 2010

Related U.S. Application Data

(60) Provisional application No. 61/140,034, filed on Dec. 22, 2008.

(51) Int. Cl.
*A01N 43/00* (2006.01)
*A01N 37/18* (2006.01)
*A61K 31/33* (2006.01)
*A61K 31/165* (2006.01)
*A61M 15/00* (2006.01)
*A61M 16/10* (2006.01)

(52) U.S. Cl. ................ 514/183; 514/622; 128/203.12

(58) Field of Classification Search ............... None
See application file for complete search history.

(56) References Cited

U.S. PATENT DOCUMENTS

| | | | |
|---|---|---|---|
| 4,624,965 | A | 11/1986 | Wenig |
| 4,729,997 | A | 3/1988 | Wenig |
| 5,116,857 | A | 5/1992 | Acher |
| 5,576,317 | A | 11/1996 | Gonsalves |
| 5,578,632 | A | 11/1996 | Tyers |
| 5,760,086 | A | 6/1998 | Psilogenis |
| 5,780,431 | A | 7/1998 | Ho et al. |
| 6,187,332 | B1 | 2/2001 | Gern et al. |
| 6,433,129 | B1 | 8/2002 | Amendola et al. |
| 6,586,563 | B1 | 7/2003 | Ortega et al. |
| 6,770,262 | B2 | 8/2004 | Lehman et al. |

FOREIGN PATENT DOCUMENTS

| | | |
|---|---|---|
| HU | 210115 B | 2/1995 |
| WO | WO-2008-096804 | 8/2008 |

OTHER PUBLICATIONS

Metoclopramide Prescribing Information (PI), FDA approved Jan. 26, 2001.*
Pramidin Prescribing Information (PI) (1997).*
Remington's Pharmaceutical Sciences (1985).*
Bateman et al., "The Pharmacokinetics of Metoclopramide in Man with Observations in the Dog," Br. J. Clin. Pharmac. 9:371-377 (1980).
Bortoli et al., "Efficacy and tolerability of metoclopramide nasal spray in the symptomatic therapy of functional dyspepsia," Curr. Therapeutic Res. 55(10):1192-1200 (1994).
Chiara et al., "Prevention of Delayed Emesis with Metoclopramide and Dexamethasone in Patients Receiving Moderately Emetogenic Cytotoxic Treatment," Anticancer Res. 15:1597-1599 (1995).
Clark et al., "Antiemetic (AE) trials to control delayed vomiting (V) following high-dose cisplatin (DDP)," Proc. Of ASCO 5:257, abstract 1005 (1986).
Clark et al., "Delayed emesis: A dilemma in antiemetic control," Support Care Cancer 1:182-185 (1993).
Crinos Industria Pharmacobiologica S.p.A. package inserts for Pramidin 10 and Pramidin 20, Apr. 1999.
Cubeddu et al., "Participation of serotonin on early and delayed emesis induced by initial and subsequent cycles of cisplatinum-based chemotherapy: Effects of antiemetics," J. Clin. Pharmacol. 33:691-697 (1993).
De Mulder et al., "Ondansetron compared with high-dose metoclopramide in prophylaxis of acute and delayed cisplatin-induced nausea and vomiting," Ann. Internal Med. 113:834-840 (1990).
Drenth and Engels, "Diabetic gastroparesis. A critical reappraisal of new treatment strategies," Drugs 44:537-553 (1992).
Du Bois et al., "Cisplatin-induced alterations of serotonin metabolism in patients with or without emesis following chemotherapy," Oncol. Rep. 2:839-842 (1995).
Gandara, "Progress in the control of acute and delayed emesis induced by cisplatin," Eur. J. Cancer 27:S9-S11 (1991).
Gandara et al., "The delayed-emesis syndrome from cisplatin: Phase III evaluation of ondansetron versus placebo," Semin. Oncol. 19:67-71 (1992).
Gralla et al., "Management of CHemotherapy-induced Nausea and Vomiting," http://www.cancernetwork.com/home/nausea/htm last viewed Oct. 11, 2002.
Gralla et al., "The management of chemotherapy-induced Nausea and Vomiting," Medical Clinics of North America (Cancer Pain) 71:289-301 (1987).
Grunberg et al., "Oral metoclopramide with or without diphenhydramine: Potential for prevention of late nausea and vomiting induced by cisplatin," J. Natl. Cancer Inst. 80:864-868 (1988).
Human Weight from Wikipedia Jun. 7, 2007, pp. 1-2, http://en.wikipedia.org/wiki/Human_weight.
Jones et al., "Comparision of dexamethasone and ondansetron in the prophylaxis of emesis induced by moderately emetogenic chemotherapy," Lancet 338:483-486 (1991).
Kris et al., "Controlling delayed vomiting: Double-blind, randomized trial comparing placebo, dexamethasone alone, and metoclopramide plus dexamethasone in patients receiving cisplatin," J. Clin. Oncol. 7:108-114 (1989).
Kris et al., "Oral ondansetron for the control of delayed emesis after cisplatin," Cancer Suppl. 70:1012-1016 (1992).
Lee et al., "Ondansetron compared with ondansetron plus metoclopramide in the prevention of cisplatin-induced emesis," J. Korean Med. Sci. 9:369-375 (1994).

(Continued)

*Primary Examiner* — Jeffrey S. Lundgren
*Assistant Examiner* — William Lee
(74) *Attorney, Agent, or Firm* — Wilson, Sonsini, Goodrich & Rosati

(57) ABSTRACT

Nasal formulations of metoclopramide, which remain stable and/or colorless upon storage over a period of time, are provided. Also provided are methods of treating disorders treatable with metoclopramide, comprising administering the nasal solutions to patients in need thereof.

29 Claims, No Drawings

OTHER PUBLICATIONS

Levitt et al., Ondansetron compared with dexamethasone and metoclopramide as antiemetics in the chemotherapy of breast cancer with cyclophosphamide, methotrexate, and fluorouracil, New Eng. J. Med. 328:1081-1084 (1993).

Li et al., "Control of cisplatin-induced delayed emesis," Chin. Med. J. (Taipei) 48:451-455 (1991).

Locatelli et al., "Tolerability and Safety of Nasally Administrered Metoclopramide (MCP) for the Prevention of CIS-Platinum (CDDP) induced Delayed Emesis," Proc. ASCO vol. 14 Mardch 1995, abstr. 1759.

Longo, W.S., and Vernava, A.M., "Prokinetic Agents for Lower Gastrointestinal Motility Disorders," Dis Colon Rectum 36:696-708 (1993).

Madej et al., "A report comparing the use of tropisetron (Navoban), a 5-HT, antagonist, with a standard antiemetic regimen of dexamethasone and metoclopramide in cisplatin-treated patients under conditions of severe emesis," Semin. Oncol. 21:3-6 (1994).

Malfertheiner, "Current concepts in dyspepsia: A world perspective," Eur. J. Gastroenterol. Hepatol. 1(Suppl. 1):S25-S29 (1999).

Mearin et al., "Placebo in Functional Dyspepsia: Symptomatic, Gastrointestinal Motor, and Gastric Sensorial Responses," Am. J. Gastroenterol. 94(1):116-125 (1999).

Medical Economics Co., 1999, PDR 53th Ed., "Physician's Desk Refernce" 2643-2645.

Medical Economics Co., 2000, PDR 54th Ed., "Physician's Desk Refernce" 2603-2605.

Metoclopramide Oral Monograph from Medscape Oct. 23, 2009, 2 pages.

Moreno et al., "Comparison of three protracted antiemetic regimens for the control of delayed emesis in cisplatin-treated patients," Eur. J. Cancer 28:1344-1347 (1992).

Navari et al., "Oral ondansetron for the control of cisplatin-induced delayed nemesis: A large, multicenter, double-blind, randomized comparative trial of ondansetron versus placebo," J. Clin. Oncol. 13:2408-2416 (1995).

Nino et al., "A randomized controlled trial of acute and delayed cisplatin-induced emesis with metoclorpramide, dexamethasone and prochlorperazine," Jpn. J. Cancer Chemother. 14:2861-2884 (1987).

O'Brien et al., "The role of metoclopramide in acute and delayed chemotherapy induced emesis: A randomized double blind trial," Br. J. Cancer 60:759-763 (1989).

Ogawa, "Metoclopramide as an antiemetic in chemotherapy," New Eng. J. Med. Correspond. 307:249-250 (1982).

Ormrod and Goa, "Intranasal Metoclopramide," reprinted from Drugs 58(2):315-324 (1999).

Perkel, M.S. et al., "Metoclopramide Therapy in Fifty-five Patients With Delayed Gastric Emptying," Am. J. Gastroenterol. 74:231-236 (1980).

Robins, product information on Reglan, obtained from on-line PDR.

Roila et al., "Cisplatin-induced delayed emesis: Pattern and prognostic factors during three subsequent cycles," Ann. Oncol. 5:585-589 (1994).

Roila et al., "Predictive factors of delayed emesis in cisplatin-treated patients and antiemetic activity and tolerability of metoclopramide or dexamethasone," Am. J. Clin. Oncol. (CCT) 14: 238-242 (1991).

Scaglione et al., "Pharmacokinetics and bioavailability of metoclopramide nasal spray versus metoclopramide intravenous in healthy volunteers and cancer patients," Arzneim.-Forsch./Drug Res. 43:986-988 (1993).

Shinkai et al., "Control of Cisplatin-induced Delayed Emesis with Metoclopramide and Dexamethasone: A Randomized Controlled Trial," Jpn. J. Clin. Oncol. 19:40-44 (1989).

Soukop et al., "Ondansetron compared with metoclopramide in the control of emesis and quality of life during repeated chemotherapy for breast cancer," Oncol. 49:295-304 (1992).

Stanghellini and Corinaldesi, "Relevance of gastrointestinal motor disturbances in functional dyspepsia," Bailliere's Clinical Gastroenterology 12(3):533-544 (1998).

Strum et al., "Management of cisplatin (DDP)-induced delayed-onset nausea (N) and vomiting (V): Preliminary results with 2 drug regimens," Proc. ASCO 4:263, abstr. C-1024 (1985).

Taylor et al., "Oral Bioavailability of High-Dose Metoclopramide," Eur. J. Clin. Pharmacol. 31:41-44 (1986).

Tomirotti et al., "Efficacy and tolerability of nasally administered compared to parenterally administered metoclopramide in the symptomatic treatment of chemotherapy-induced emesis in cancer outpatients," Support Care Cancer 2:389-392 (1994).

Vivien et al., "Nasal Absorption of Metoclopramide Administered to Man," Eur. J. Pharmaceutics and Biopharmaceutics 40(4):228-231 (1994).

Vogt et al., "Oral Medium-Dosed Metoclopramide versus Placebo as Highly Effective Antiemetic Prophylaxis in In- and Outpatients on Noncisplatin Chemotherapy," Oncol. 50:81-85 (1993).

EP01922935 Supplementary Partial Search Report dated Jul. 13, 2007.

EP97915060 Supplementary Search Report dated Jan. 23, 2004.

PCT/US01/10356 Search Report dated Jun. 13, 2001.

PCT/US97/03974 Search Report dated Jun. 25, 1997.

PCT/US09/069298 Search Report and Written Opinion mailed Sep. 3, 2010.

* cited by examiner

US 8,334,281 B2

NASAL FORMULATIONS OF METOCLOPRAMIDE

This application claims priority under 35 U.S.C. §119(e) from U.S. Provisional Patent No. 61/140,034, filed Dec. 22, 2008, which is incorporated herein in its entirety.

BACKGROUND OF THE INVENTION

Metoclopramide is approved in the United States in oral solution, oral tablet and injectable solution forms. Wenig has suggested the use of nasally-administered metoclopramide for the treatment of emesis or nausea. (See U.S. Pat. No. 4,624,965, issued Nov. 25, 1986, which is incorporated by reference herein in its entirety.) Psilogenis has suggested nasal administration of metoclopramide for the treatment of delayed onset emesis. (See U.S. Pat. No. 5,760,086, issued Jun. 2, 1998, incorporated herein by reference in its entirety.) Lehman et al. have proposed administering nasal formulations of metoclopramide for the treatment of gastroparesis. (See U.S. Pat. No. 6,770,262, issued Aug. 3, 2004, incorporated herein by reference in its entirety.)

SUMMARY OF THE INVENTION

The inventors have discovered that, though previously-described nasal solutions of metoclopramide are substantially free of color or colorless when initially formulated, they tend to become discolored on storage. In particular, the inventors have determined that under accelerated stability conditions, which are designed to simulate long-term storage conditions typical for nasal solutions, the previously-described nasal solutions of metoclopramide tend to take on a yellow-to-brown color. Accordingly, the inventors have determined that there is a need for an nasal solution of metoclopramide that is stable over time. The inventors have also determined that there is a need for an nasal solution of metoclopramide that is substantially free of color when formulated, and that remains substantially free of color over time. Accordingly, the present disclosure concerns pharmaceutical compositions for nasal administration that are stable upon long-term storage, that remain substantially free of color, and/or that remain substantially clear upon long-term storage. Further characteristics, uses and advantages of the invention will become clear to the person having skill in the art upon consideration of the following disclosure.

Some embodiments described herein provide a pharmaceutical composition comprising metoclopramide, or a pharmaceutically-acceptable salt thereof, a citrate buffer, and benzalkonium chloride; wherein the composition is stable; and wherein the composition has a citrate concentration ([citrate]=[citric acid]+[dihydrogen citrate ion]+[hydrogen citrate ion]+[citrate ion]) of at least about 10 millimolar.

Some embodiments described herein provide a pharmaceutical composition comprising metoclopramide, or a pharmaceutically-acceptable salt thereof, a citrate buffer, and benzalkonium chloride; wherein the composition is substantially free of color; and wherein the composition has a citrate concentration ([citrate]=[citric acid]+[dihydrogen citrate ion]+[hydrogen citrate ion]+[citrate ion]) of at least about 10 millimolar.

Some embodiments described herein provide a pharmaceutical composition comprising metoclopramide, or a pharmaceutically-acceptable salt thereof, a buffer, and benzalkonium chloride; wherein the composition is stable; and wherein the composition has a pH of above about 4.5.

Some embodiments described herein provide a pharmaceutical composition comprising metoclopramide, or a pharmaceutically-acceptable salt thereof, a citrate buffer, and benzalkonium chloride; wherein the composition is substantially free of color; and wherein the composition has a pH of above about 4.5.

Some embodiments described herein provide a pharmaceutical composition comprising metoclopramide, or a pharmaceutically-acceptable salt thereof, a citrate buffer, and benzalkonium chloride; wherein the composition is substantially clear; and wherein the composition has a pH of above about 4.5.

Some embodiments described herein provide a pharmaceutical composition comprising metoclopramide, or a pharmaceutically-acceptable salt thereof, a citrate buffer, and optionally less than about 1% w/v benzyl alcohol; wherein the composition is stable; and wherein the composition has a citrate concentration ([citrate]=[citric acid]+[dihydrogen citrate ion]+[hydrogen citrate ion]+[citrate ion]) of at least about 10 millimolar. In some embodiments, the composition comprises about 0.75% w/v benzyl alcohol or less, or about 0.5% w/v benzyl alcohol or less.

Some embodiments described herein provide a pharmaceutical composition comprising metoclopramide, or a pharmaceutically-acceptable salt thereof, a citrate buffer, and optionally less than about 1% w/v benzyl alcohol; wherein the composition is free of color; and wherein the composition has a citrate concentration ([citrate]=[citric acid]+[dihydrogen citrate ion]+[hydrogen citrate ion]+[citrate ion]) of at least about 10 millimolar. In some embodiments, the composition comprises about 0.75% w/v benzyl alcohol or less, or about 0.5% w/v benzyl alcohol or less.

Some embodiments described herein provide a pharmaceutical composition comprising metoclopramide, or a pharmaceutically-acceptable salt thereof, a citrate buffer, and optionally less than about 1% w/v benzyl alcohol; wherein the composition is substantially clear; and wherein the composition has a citrate concentration ([citrate]=[citric acid]+[dihydrogen citrate ion]+[hydrogen citrate ion]+[citrate ion]) of at least about 10 millimolar. In some embodiments, the composition comprises about 0.75% w/v benzyl alcohol or less, or about 0.5% w/v benzyl alcohol or less.

Some embodiments described herein provide for use of a metoclopramide solution as described herein, e.g. in one or more of paragraphs [0003]-[0012], for preparation of a medicament for the treatment of a disorder that is treatable with metoclopramide.

Some embodiments described herein provide a manufacture comprising a metoclopramide pharmaceutical composition as described herein, e.g. in one or more of paragraphs [0003]-[0012], and a means for nasal administration of said composition to a patient.

Additional embodiments, features and advantages will become apparent upon consideration of the following detailed description of the invention.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

The invention is directed toward nasally-administrable solutions comprising metoclopramide, which are stable upon storage, especially long-term storage. The invention is further directed toward nasally-administrable metoclopramide solutions, which are clear and/or colorless. The invention is further directed toward nasally-administrable metoclopramide solutions, which are clear and/or colorless when initially formulated (compounded) especially after filled in pharmaceutical device glass containers, and which remain substantially clear and/or colorless upon storage, e.g. upon long-term storage. Substantial clarity and colorlessness may be evaluated by one of the methods described herein.

The inventors are believed to be the first to provide a practical solution to the problem of eventual discoloration of previously-described nasal metoclopramide compositions. The previously-described nasal metoclopramide solutions tend to become discolored upon storage, even when they are clear as initially formulated. This tendency is especially pronounced when the previously-described nasal metoclopramide solutions are subjected to accelerated conditions from about 25° C. to 40° C. or higher, e.g. at 40° C./75% RH ("RH" being relative humidity). While it is not known at this time what causes the previously-known nasal formulations of metoclopramide to become discolored upon storage, especially under accelerated conditions, it is considered undesirable for a solution that is clear and colorless when originally formulated to become colored upon storage. Given the scrutiny applied to pharmaceutical compositions by pharmaceutical industry regulatory bodies, it is considered necessary to reduce or eliminate discoloration of pharmaceutical compositions if at all possible, at least over the period of time during which, and under the conditions at which, they are likely to be stored. In order to increase patient acceptance of metoclopramide solutions, the present inventors increased the pH of previous metoclopramide solutions closer to neutral, only to find that the increase in pH led to increased discoloration of the metoclopramide solutions. In addition to identifying the problem of increased discoloration upon storage of higher pH formulations of previously-described solutions of metoclopramide, the inventors are also the first to have provided a solution to the problem of discoloration. Factors that can affect stability of aqueous solutions of metoclopramide include the specific buffer, the pH of the buffered solution, and the presence or absence of benzyl alcohol and/or benzalkonium chloride. An additional factor in discoloration of metoclopramide solutions is exposure of the solution to light, especially during long-term storage.

Thus, in some embodiments described herein there is provided a pharmaceutical composition comprising metoclopramide (or a pharmaceutically-acceptable salt thereof), citrate buffer and benzalkonium chloride having a pH of at least about 5.

Some embodiments described herein provide a pharmaceutical composition comprising metoclopramide, or a pharmaceutically-acceptable salt thereof, a citrate buffer, and benzalkonium chloride; wherein the composition is stable; and wherein the composition has a citrate concentration ([citrate]=[citric acid]+[dihydrogen citrate ion]+[hydrogen citrate ion]+[citrate ion]) of at least about 10 millimolar. Other embodiments described herein provide a pharmaceutical composition comprising metoclopramide, or a pharmaceutically-acceptable salt thereof, a citrate buffer, and benzalkonium chloride; wherein the composition is substantially free of color; and wherein the composition has a citrate concentration ([citrate]=[citric acid]+[dihydrogen citrate ion]+[hydrogen citrate ion]+[citrate ion]) of at least about 10 millimolar. Other embodiments described herein provide a pharmaceutical composition comprising metoclopramide, or a pharmaceutically-acceptable salt thereof, a citrate buffer, and benzalkonium chloride; wherein the composition is substantially clear; and wherein the composition has a citrate concentration ([citrate]=[citric acid]+[dihydrogen citrate ion]+[hydrogen citrate ion]+[citrate ion]) of at least about 10 millimolar. In some embodiments, the composition has a citrate concentration ([citrate]=[citric acid]+[dihydrogen citrate ion]+[hydrogen citrate ion]+[citrate ion]) of at least about 10 millimolar, at least about 15 millimolar, at least about 20 millimolar, about 10-100 millimolar, about 10-50 millimolar, about 10-25 millimolar, about 10-20 millimolar, about 10-15 millimolar, about 15-100 millimolar, about 15-50 millimolar, about 15-25 millimolar or about 15-20 millimolar. In some embodiments, the pharmaceutical composition has a starting pH of at least about 4.5, at least about 4.6, at least about 4.7, at least about 4.8, at least about 4.9, at least about 5.0, at least about 5.1 or at least about 5.2, in a range of about 4.5-6.0, in a range of about 4.6-5.9, in a range of about 4.7-5.8, in a range of about 4.8-5.7, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9 or about 6.0. In some embodiments, the composition is substantially free of any additional antioxidant. In some embodiments, the composition further comprises at least one member of the group consisting of a salt, EDTA, sorbitol, a sugar (including a reduced sugar, such as sorbitol) or a flavoring agent. In some embodiments, the pharmaceutical composition has a concentration of metoclopramide, or a pharmaceutically-acceptable salt thereof, of from about 20.0% (w/v) to about 30.0% (w/v). In some embodiments, the pharmaceutical composition has a concentration of benzalkonium chloride from about 0.005% (w/v) to about 0.05% (w/v). In some embodiments, the pharmaceutical composition has an osmolality of from about 500 mOsm/kg to about 1400 mOsm/kg. In some embodiments, the osmolality is from about 500 mOsm/kg to about 1000 mOsm/kg. In some embodiments, the osmolality is from about 1000 mOsm/kg to about 1400 mOsm/kg. In some embodiments, the composition remains stable on storage at a temperature of about 25° C. to about 40° C. for at least about 4 weeks, at least about 6 weeks, at least about 8 weeks, at least about 10 weeks, at least about 12 weeks, at least about 16 weeks, at least about 20 weeks or at least about 6 months. In some embodiments, the composition remains substantially free of color on storage at a temperature of about 25° C. to about 40° C. for at least about 4 weeks, at least about 6 weeks, at least about 8 weeks, at least about 10 weeks, at least about 12 weeks, at least about 16 weeks, at least about 20 weeks or at least about 6 months. In some embodiments, the composition remains substantially clear on storage at a temperature of about 25° C. to about 40° C. for at least about 4 weeks, at least about 6 weeks, at least about 8 weeks, at least about 10 weeks, at least about 12 weeks, at least about 16 weeks, at least about 20 weeks or at least about 6 months.

Some embodiments described herein provide a pharmaceutical composition comprising metoclopramide, or a pharmaceutically-acceptable salt thereof, a buffer, and benzalkonium chloride; wherein the composition is stable; and wherein the composition has a pH of above about 4.5. Some embodiments described herein provide a pharmaceutical composition comprising metoclopramide, or a pharmaceutically-acceptable salt thereof, a citrate buffer, and benzalkonium chloride; wherein the composition is substantially free of color; and wherein the composition has a pH of above about 4.5. Some embodiments described herein provide a pharmaceutical composition comprising metoclopramide, or a pharmaceutically-acceptable salt thereof, a citrate buffer, and benzalkonium chloride; wherein the composition is substantially clear; and wherein the composition has a pH of above about 4.5. In some embodiments, the pharmaceutical composition has a starting pH of at least about 4.6, at least about 4.7, at least about 4.8, at least about 4.9, at least about 5.0, at least about 5.1 or at least about 5.2, in a range of about 4.5-6.0, in a range of about 4.6-5.9, in a range of about 4.7-5.8, in a range of about 4.8-5.7, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9 or about 6.0. In some embodiments, the composition remains stable on storage at a temperature of about 25° C. to about 40° C. for at least about 4 weeks, at least about 6 weeks, at least about 8 weeks, at least about 10 weeks, at least about 12 weeks, at least about 16 weeks, at least about 20 weeks or at least about 6 months. In some embodiments, the composition remains substantially free of color on storage at a temperature of about 25° C. to about 40° C. for at least about 4 weeks, at least about 6 weeks, at least about 8 weeks, at least about 10 weeks, at least about 12 weeks, at least about 16 weeks, at least about 20 weeks or at least about 6 months. In some embodiments, the composition remains substantially clear on storage at a temperature of about 25° C. to about 40° C. for at least about 4 weeks, at least about 6 weeks, at least about 8 weeks, at least about 10 weeks, at least about 12 weeks, at least about 16 weeks, at least about 20 weeks or at least about 6 months. In some embodiments, the buffer is selected from the group consisting of citric acid/phosphate, acetate, barbital, borate, Britton-Robinson, cacodylate, citrate, collidine, formate, maleate, McIlvaine, phosphate, Prideaux-Ward, succinate, citrate-phosphate-borate (Teorell-Stanhagen), veronal acetate, MES (2-(N-morpholino)ethanesulfonic acid), BIS-TRIS (bis(2-hydroxyethyl)iminotris(hydroxymethyl)methane), ADA (N-(2-acetamido)-2-iminodiacetic acid), ACES (N-(carbamoylmethyl)-2-aminoethanesulfonaic acid), PIPES (piperazine-N,N'-bis(2-ethanesulfonic acid)), MOPSO (3-(N-morpholino)-2-hydroxy-propanesulfonic acid), BIS-TRIS PROPANE (1,3-bis(tris(hydroxymethyl)methylamino)propane), BES (N,N-bis(2-hydroxyethyl)-2-aminoethanesulfonaic acid), MOPS (3-(N-morpholino)propane-sulfonic acid), TES (N-tris(hydroxymethyl)methyl-2-aminoethanesulfonic acid), HEPES (N-(2-hydroxyethyl)piperazine-N'-(2-ethanesulfonic acid), DIPSO (3-(N,N-bis(2-hydroxyethyl)amino)-2-hydroxypropanesulfonic acid), MOBS (4-(N-morpholino)butanesulfonic acid), TAPSO (3-(N-tris(hydroxymethyl)methylamino)-2-hydroxy-propanesulfonic acid), tris (hydroxymethylamino-methane, HEPPSO (N-(2-hydroxyethyl)piperazine-N'-(2-hydroxypropanesulfonic acid), POPSO (piperazine-N,N'-bis(2-hydroxypropanesulfonic acid)), TEA (triethanolamine), EPPS (N-(2-hydroxyethyl)piperazine-N'-(3-propane-sulfonic acid), TRICINE (N-tris(hydroxymethyl)methyl-glycine), GLY-GLY (glycylglycine), BICINE (N,N-bis(2-hydroxyethyl)glycine), HEPBS (N-(2-hydroxyethyl)piperazine-N'-(4-butanesulfonic acid)), TAPS(N-tris(hydroxy-methyl)methyl-3-aminopropanesulfonic acid), or AMPD (2-amino-2-methyl-1,3-propanediol) buffer.

Some embodiments described herein provide a pharmaceutical composition comprising metoclopramide, or a pharmaceutically-acceptable salt thereof, and citric acid as a stabilizer, wherein the composition is stable. Some embodiment described herein provide a pharmaceutical composition comprising metoclopramide, or a pharmaceutically-acceptable salt thereof, and citric acid as a stabilizer, wherein the composition is substantially free of color. Some embodiments described herein provide a pharmaceutical composition comprising metoclopramide, or a pharmaceutically-acceptable salt thereof, and citric acid as a stabilizer, wherein the composition is substantially clear. In some embodiments, the composition has a citric acid concentration of at least about 5 millimolar, at least about 10 millimolar, at least about 15 millimolar, at least about 20 millimolar, about 5-100 millimolar, about 5-50 millimolar, about 5-25 millimolar, about 5-20 millimolar, about 5-15 millimolar, about 5-10 millimolar, about 10-100 millimolar, about 10-50 millimolar, about 10-25 millimolar, about 10-20 millimolar, about 10-15 millimolar, about 15-100 millimolar, about 15-50 millimolar, about 15-25 millimolar or about 15-20 millimolar. In some embodiments, the composition is substantially free of any additional antioxidant. In some embodiments, the composition further comprises at least one member of the group consisting of a salt, EDTA, sorbitol, a sugar (including a reduced sugar, such as sorbitol) or a flavoring agent. In some embodiments, the pharmaceutical composition has a concentration of metoclopramide, or a pharmaceutically-acceptable salt thereof, of from about 20.0% (w/v) to about 30.0% (w/v). In some embodiments, the composition further contains benzalkonium chloride at a concentration from about 0.005% (w/v) to about 0.05% (w/v). In some embodiments, the pharmaceutical composition has an osmolality of from about 500 mOsm/kg to about 1400 mOsm/kg. In some embodiments, the osmolality is from about 500 mOsm/kg to about 1000 mOsm/kg. In some embodiments, the osmolality is from about 1000 mOsm/kg to about 1400 mOsm/kg. In some embodiments, the composition remains stable on storage at a temperature of about 25° C. to about 40° C. for at least about 4 weeks, at least about 6 weeks, at least about 8 weeks, at least about 10 weeks, at least about 12 weeks, at least about 16 weeks, at least about 20 weeks or at least about 6 months. In some embodiments, the composition remains substantially free of color on storage at a temperature of about 25° C. to about 40° C. for at least about 4 weeks, at least about 6 weeks, at least about 8 weeks, at least about 10 weeks, at least about 12 weeks, at least about 16 weeks, at least about 20 weeks or at least about 6 months. In some embodiments, the composition remains substantially clear on storage at a temperature of about 25° C. to about 40° C. for at least about 4 weeks, at least about 6 weeks, at least about 8 weeks, at least about 10 weeks, at least about 12 weeks, at least about 16 weeks, at least about 20 weeks or at least about 6 months.

Some embodiments described herein provide a pharmaceutical composition comprising metoclopramide, or a pharmaceutically-acceptable salt thereof, a citrate buffer, and optionally less than about 1% w/v benzyl alcohol; wherein the composition is stable; and wherein the composition has a citrate concentration ([citrate]=[citric acid]+[dihydrogen citrate ion]+[hydrogen citrate ion]+[citrate ion]) of at least about 10 millimolar. Some embodiments described herein provide a pharmaceutical composition comprising metoclopramide, or a pharmaceutically-acceptable salt thereof, a citrate buffer, and optionally less than about 1% w/v benzyl alcohol; wherein the composition is substantially free of color; and wherein the composition has a citrate concentration ([citrate]=[citric acid]+[dihydrogen citrate ion]+[hydrogen citrate ion]+[citrate ion]) of at least about 10 millimolar. Some embodiments described herein provide a pharmaceutical composition comprising metoclopramide, or a pharmaceutically-acceptable salt thereof, a citrate buffer, and optionally less than about 1% w/v benzyl alcohol; wherein the composition is substantially clear; and wherein the composition has a citrate concentration ([citrate]=[citric acid]+[dihydrogen citrate ion]+[hydrogen citrate ion]+[citrate ion]) of at least about 10 millimolar. In some embodiments, the concentration of benzyl alcohol is about 0.01 to about 0.8% w/v, about 0.01 to about 0.5% w/v, about 0.01 to about 0.25% w/v, about 0.01 to about 0.1% w/v, about 0.01 to about 0.05% w/v. In some embodiments, the pharmaceutical composition remains stable when stored in a package in which the composition is not in contact with oxygen. In some embodiments, the pharmaceutical composition does not discolor when stored in a package in which the composition is not in contact with oxygen. In some embodiments, the pharmaceutical composition remains clear when stored in a package in which the composition is not in contact with oxygen. In some embodiments, the composition remains stable at a temperature of about 25° C. to about 40° C. for at least about 4 weeks, at least about 6 weeks, at least about 8 weeks, at least about 10 weeks, at least about 12 weeks, at least about 16 weeks, at least about 20 weeks or at least about 6 months. In some embodiments, the composition remains free of color at a temperature of about 25° C. to about 40° C. for at least about 4 weeks, at least about 6 weeks, at least about 8 weeks, at least about 10 weeks, at least about 12 weeks, at least about 16 weeks, at least about 20 weeks or at least about 6 months. In some embodiments, the composition remains clear at a temperature of about 25° C. to about 40° C. for at least about 4 weeks, at least about 6 weeks, at least about 8 weeks, at least about 10 weeks, at least about 12 weeks, at least about 16 weeks, at least about 20 weeks or at least about 6 months. In some embodiments, the composition has a citrate concentration ([citrate]=[citric acid]+[dihydrogen citrate ion]+[hydrogen citrate ion]+[citrate ion]) of at least about 10 millimolar, at least about 15 millimolar, at least about 20 millimolar, about 10-100 millimolar, about 10-50 millimolar, about 10-25 millimolar, about 10-20 millimolar, about 10-15 millimolar, about 15-100 millimolar, about 15-50 millimolar, about 15-25 millimolar or about 15-20 millimolar. In some embodiments, the pharmaceutical composition has a starting pH of at least about 4.5, at least about 4.6, at least about 4.7, at least about 4.8, at least about 4.9, at least about 5.0, at least about 5.1 or at least about 5.2, in a range of about 4.5-6.0, in a range of about 4.6-5.9, in a range of about 4.7-5.8, in a range of about 4.8-5.7, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9 or about 6.0. In some embodiments, the composition is substantially free of any additional antioxidant. In some embodiments, the composition further comprises at least one member of the group consisting of a salt, EDTA, sorbitol, a sugar (including a reduced sugar, such as sorbitol) or a flavoring agent. In some embodiments, the pharmaceutical composition has a concentration of metoclopramide, or a pharmaceutically-acceptable salt thereof, of from about 20.0% (w/v) to about 30.0% (w/v). In some embodiments, the pharmaceutical composition has a concentration of benzalkonium chloride from about 0.005% (w/v) to about 0.05% (w/v). In some embodiments, the pharmaceutical composition has an osmolality of from about 500 mOsm/kg to about 1400 mOsm/kg. In some embodiments, the osmolality is from about 500 mOsm/kg to about 1000 mOsm/kg. In some embodiments, the osmolality is from about 1000 mOsm/kg to about 1400 mOsm/kg.

Some embodiments provide a method of treating a patient, comprising administering to the patient an effective amount of a composition as described herein, e.g. in one or more of paragraphs [0019]-[0023]. In some embodiments, the patient has a disorder that is treatable with metoclopramide.

In some embodiments, the disorder that is treatable with metoclopramide is at least one member of the group consisting of gastroparesis, emesis, delayed emesis and nausea. In some embodiments, the disorder is gastroparesis. In some embodiments, the disorder is emesis or delayed emesis. In some embodiments, the disorder is nausea. In some embodiments, the composition is administered as one spray in one nostril per day. In some embodiments, each spray contains about 10 mg to about 20 mg of metoclopramide. In some embodiments, each spray contains about 10 mg, about 15 mg or about 20 mg of metoclopramide. In some embodiments, the composition is administered as two sprays, one in each nostril, per day. In some embodiments, each spray contains about 5 mg to about 10 mg of metoclopramide. In some embodiments, each spray contains about 5 mg, about 6 mg, about 7 mg, about 8 mg, about 9 mg or about 10 mg of metoclopramide.

Some embodiments described herein provide for use of a metoclopramide solution as described herein, e.g. in one or more of paragraphs [0019]-[0023] for preparation of a medicament for the treatment of a disorder that is treatable with metoclopramide. In some embodiments, the disorder that is treatable with metoclopramide is at least one member of the group consisting of gastroparesis, emesis, delayed emesis and nausea. In some embodiments, the disorder is gastroparesis. In some embodiments, the disorder is emesis or delayed emesis. In some embodiments, the disorder is nausea. In some embodiments, the medicament is contained in a nasal administration device, In some embodiments, the nasal administration device is adapted or adaptable to deliver a pre-defined dose of metoclopramide per spray. In some embodiments, the predefined dose of metoclopramide is about 1 mg to about 25 mg per spray. In some embodiments, the predefined dose of metoclopramide is about 5 mg, about 10 mg, about 15 mg or about 20 mg of metoclopramide per spray. In some embodiments, the predefined dose of metoclopramide is about 5 mg, about 6 mg, about 7 mg, about 8 mg, about 9 mg, about 10 mg, about 15 mg or about 20 mg of metoclopramide per spray.

Some embodiments described herein provide a manufacture comprising a metoclopramide pharmaceutical composition as described herein, e.g. in one or more of paragraphs [0019]-[0023], and a means for nasal administration of said composition to a patient. In some embodiments, the means for nasal administration comprises a reservoir that contains the composition, a pump in fluid communication with the composition in the reservoir and a nozzle in fluid communication with the pump, wherein activation of the pump withdraws a predetermined amount of said composition from the reservoir and causes said predetermined amount of said composition to be expelled from said nozzle. In some embodiments, the predetermined amount of composition is about 10 μL to about 500 μL, about 50 μL to about 250 μL, about 50 μL, about 75 μL, about 100 μL, about 125 μL, about 150 μL, about 175 μL, about 200 μL, about 225 μL or about 250 μL per activation ("spray"). In order to combat the deleterious effects of light on metoclopramide, the manufacture may conveniently include a container, especially an opaque container, i.e. a container that is at least partially or completely impervious to light. In some embodiments, a suitable opaque container will be brown or amber, especially brown or amber glass. In other embodiments, the opaque container will be an opaque polymer container, such as is commonly used in the pharmaceutical arts.

DEFINITIONS

As used herein, the term "starting pH" is the pH of a solution at a time prior to, or shortly after (<1d), the solution being dispensed into a vial or other unit dosage form suitable for nasal administration.

Citric acid (IUPAC Name 2-hydroxypropane-1,2,3-tricarboxylic acid) is an organic acid having three carboxylic acid groups. In water, citric acid partially dissociates to form dihydrogen citrate ion, hydrogen citrate ion and citrate ion. The proportions of citric acid and its conjugate anions in a solution influence the pH of the solution, which is defined as $-\log_{10}[H_3O]$.

As used herein the term "citrate" refers to the anion of citric acid in all its forms, i.e. fully protonated (citric acid), partially dissociated (dihydrogen citrate ion: $C_3H_7O(COO)_3^-$, hydrogen citrate ion: $C_3H_6O(COO)_3^{2-}$) and fully dissociated (citrate ion: $C_3H_5O(COO)_3^{3-}$) forms. Where a particular ion of citric acid is intended, it will be so specified, otherwise the term "citrate" by itself refers to the sum of all protonated and ionic forms of citrate. Thus, [citrate]=$[C_3H_8O(COO)_3]$+$[C_3H_7O(COO)_3^-]$+$[C_3H_6O(COO)_3^{2-}]$+$[C_3H_5O(COO)_3^{3-}]$=[citric acid]+[dihydrogen citrate ion]+[hydrogen citrate ion]+[citrate ion].

Benzalkonium chloride (also known as "alkyldimethylbenzylammonium chloride", "ADBAC" or simply "BAC") is a mixture of alkylbenzyldimethylammonium chlorides of various even-numbered alkyl chain lengths. BAC, as used herein, has the formula:

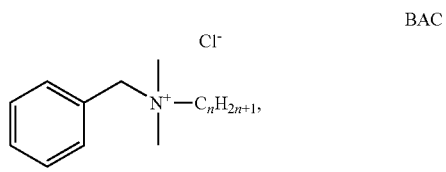

BAC wherein n is 2, 4, 6, 8, 10, 12, 14, 16, 18, 20, etc; in some preferred embodiments, n is 8 to 18. Benzalkonium chloride USP NF is generally used as a 50% w/v solution of BAC in water. Thus, in some embodiments, recited values of benzalkonium chloride (BAC) used herein refer to a 50% w/v solution of BAC in water. However, the values recited in the claims represent the concentration (% w/v) of BAC in the final solution.

A nasal solution is substantially free of color when it is suitable for pharmaceutical administration, especially after storage, and in particular after storage at accelerated conditions (e.g. 40° C./75% RH) for up to about 8 weeks, 6 months, or more. Where a particular degree of clarity is intended, such will be recited with specificity. The United States Pharmacopoeia (USP) provides exemplary methodologies for determining the color of solutions, e.g. in 32 USP, NF 27, which is incorporated herein by reference. Color may be qualitatively judged by comparing a nasal solution to one or more color reference standards. Suitable reference standards may be produced as set forth in the 32 USP <631>. An example of a suitable reference standard is reference standard "E" described in 32 USP <631>. Another example of a suitable reference standard is a 50:50 dilution of reference standard "E" with water. Other examples of reference standards include reference standards A, B or C described in 32 USP <631>. In some instances, color may be quantitatively measured against a yellowish reference standard, such as 0.0005 M iodine in water—at 450 nm. The absorbance of iodine under these conditions has been measured to be 0.2440±0.0017 absorbance units. The percent optical density (% O.D.) is related to the absorbance of the iodine solution (Standard) as discussed herein below. Generally, a 200 mg/mL solution of metoclopramide hydrochloride that is substantially free of color after storage at 40° C./75% RH for 8 weeks has a % O.D. of less than about 25%, e.g. less than about 23%, at 450 nm as compared to a 0.0005 M iodine in water solution. In some embodiments, a 200 mg/mL solution of metoclopramide hydrochloride that is substantially free of color after storage for 8 weeks under 40° C./75% RH conditions, has an absorbance at 450 nm of less than 0.07 absorbance units, and especially less than about 0.06 absorbance units.

$$\% \ OD = \frac{\text{Absorbance of Sample} \times 100\%}{\text{Absorbance of Standard}}$$

wherein:

Absorbance of Standard is the absorbance at 450 nM of 0.0005 M iodine in water; and Absorbance of Sample is the absorbance at 450 nM of a metoclopramide hydrochloride sample as described herein, e.g. in one or more of paragraphs [0020]-[0023].

In some embodiments, a "substantially free of color", "substantially clear" or "stable" metoclopramide solution is one that is clear to pale yellow when compared to a standard prepared according to the following standard "E", which is set forth at 32 USP <631>. The standard matching solution is prepared by combining 4.0 mL of cobaltous chloride colorometric solution (USP CS), 12.0 mL of ferric chloride colorometric solution (USP CS), and 3.0 mL of cupric sulfate solution (USP CS) into a 50 mL volumetric flask and making the flask up to 50 mL with deionized water. Color determination is conducted by pipetting 5.0 mL of standard matching solution into a 20 mL scintillation vial (about 15 mm height), pipetting 5.0 mL of sample solution into a separate 20 mL scintillation vial (about 15 mm height) and comparing the color of the two solutions under diffused day light against a vertical white background. In some embodiments, a sample whose color is clear, lighter than the standard or the same color as the standard is considered "substantially free of color", "substantially clear" or "stable" as described herein. Objectivity may be ensured by having the color of a test solution evaluated against the standard solution by more than one person.

In some embodiments, a "substantially free of color", "substantially clear" or "stable" metoclopramide solution is one that is clear to pale yellow when compared to a standard prepared according to the following standard "C", which is set forth at 32 USP <631>. The standard matching solution is prepared by combining 1.0 mL of cobaltous chloride colorometric solution (USP CS), 4.0 mL of ferric chloride colorometric solution (USP CS), and 1.0 mL of cupric sulfate solution (USP CS) into a 50 mL volumetric flask and making the flask up to 50 mL with deionized water. Color determination is conducted by pipetting 5.0 mL of standard matching solution into a 20 mL scintillation vial (about 15 mm height), pipetting 5.0 mL of sample solution into a separate 20 mL scintillation vial (about 15 mm height) and comparing the color of the two solutions under diffused day light against a vertical white background. In some embodiments, a sample whose color is clear, lighter than the standard or the same color as the standard is considered "substantially free of color", "substantially clear" or "stable" as described herein.

Objectivity may be ensured by having the color of a test solution evaluated against the standard solution by more than one person.

In some embodiments herein, a stable metoclopramide solution is a solution in which the solution is pharmaceutically acceptable, e.g. wherein the active pharmaceutical ingredient meets the specifications of a governmental pharmaceutical purity and efficacy regulatory body, such as the United States Food and Drug Administration (FDA). In particular embodiments, a stable metoclopramide solution is a solution of metoclopramide which, after storage at 40° C./75% RH for 8 weeks, has a percent optical density (% O.D.) at 450 nm, relative to 0.0005 M iodine in water solution, of less than about 24% O.D. per 200 mg/mL of metoclopramide. Stability may be measured under accelerated conditions, such as high temperature and/or high humidity. In some embodiments, a stable metoclopramide solution is a solution of metoclopramide which, when stored at 40° C./75% RH, demonstrates an average change in percent optical density (% O.D.) at 450 nm, relative to 0.0005 M iodine in water solution, of less than about 2% O.D. per week per 200 mg/mL of metoclopramide. In some embodiments, the change in % O.D. is measured between weeks 1 and 8 of storage at 40° C./75% RH. In some embodiments, a stable metoclopramide solution is a solution of metoclopramide which, when stored at 40° C./75% RH, demonstrates an average change in percent optical density (% O.D.) at 450 nm, relative to 0.0005 M iodine in water solution, of less than about 1.8% O.D. per week per 200 mg/mL of metoclopramide. In some embodiments, the change in % O.D. is measured between weeks 1 and 8 of storage at 40° C./75% RH. In some embodiments, the change in absorbance at 450 nm for a stable metoclopramide solution of 200 mg/mL, measured between weeks 1 and 8 of storage at 40° C./75% RH, is less than about 0.004 absorbance units per week.

As used herein, "substantially free of any additional antioxidant" means that the solution contains no additional antioxidants other than those that are positively recited. In some embodiments, a solution may contain citrate, as defined herein, and be substantially free of any additional antioxidant.

As used herein, "as an antioxidant", especially in reference to citric acid, means that the ingredient is added in order to impart its antioxidant value to the solution, and no conjugate salt of the ingredient (e.g. citric acid) or other pH adjuster (e.g. sodium hydroxide) is added to bring the solution to a particular pH. Thus, use of an ingredient "as an oxidant" is distinguished from use of the same ingredient as a buffer, where a particular pH or pH range is achieved by adding specific amounts of both acid and conjugate salt or base. This reflects the inventors' discovery that in some embodiments, addition of an acid ingredient, such as citric acid, to a solution results in stabilization of metoclopramide and protection of the solution against color change, and that in some embodiments it is not necessary to counter the acidity of said acid ingredient with a conjugate salt, or to form the conjugate salt in situ with addition of base, in order to achieve this stability and tendency not to change color.

As used herein, the indefinite articles "a" and "an" mean "at least one" unless otherwise stated. Likewise, the definite article "the", unless otherwise indicated, means "at least the" where the context permits or demands it to be open-ended.

As used herein, a "nasal administration device" is a device capable of administering a dose of a composition comprising metoclopramide into the nose of a patient. In some embodiments, the nasal administration device is an atomizer, comprising a reservoir adapted to contain the metoclopramide solution and a pump adapted to draw a predetermined amount of the metoclopramide solution from the reservoir dispense the predetermined amount of metoclopramide solution through an atomizing nozzle and into at least one nostril of a patient. Suitable nasal administration devices are commercially available As used herein, the term "spray" indicates an atomized volume of liquid expelled from a nozzle of a nasal administration device upon a single activation of the nasal administration device. In general, each spray is administered into a single nostril of a patient.

As used herein, "metoclopramide" means metoclopramide (-amino-5-chloro-N-(2-(diethylamino)ethyl)-2-methoxybenzamide) or a pharmaceutically acceptable salt thereof. Where reference is made to a particular mass of metoclopramide, the recited mass is that of the free base of metoclopramide, unless otherwise specified.

Buffers

In some embodiments, the nasal formulations of metoclopramide must have a pH of at least about 4.5, at least about 4.6, at least about 4.7, at least about 4.8, at least about 4.9, at least about 5, at least about 5.1 or at least about 5.2. In order to achieve and maintain an appropriate pH, it is considered necessary to use a buffer. Generally, a buffer comprises a combination of an acid (sometimes abbreviated HA) and a complementary base ($A^-$). A buffer may be referred to by reciting the acid or the base that forms one half of the complementary acid-base (HA-A) pair. For example, acetic acid has the formula: $CH_3C(O)OH$, and forms a buffer with its complementary base, acetate ion, $CH_3C(O)O^-$ in aqueous solution. The buffer so formulated may be referred to as an acetate buffer or as an acetic acid buffer. The person having skill in the art will recognize that when the term buffer is used with either the acid or its complementary base, it refers to a mixture of the acid and the free base in solution. Thus, a citrate buffer (or citric acid buffer) refers to a mixture of citric acid and citrate ion. Since citric acid has three titratable groups, a citrate buffer (or citric acid buffer) can refer to a mixture of citric acid, and one or more of the complementary bases resulting from removal of one, two or three of the protons.

In some embodiments described herein, it is desirable to combine citric acid monohydrate and sodium citrate dihydrate in the nasal preparation in proportions suitable to provide a stable pH (+/−0.2 pH units) of about 4.5 and above, about 4.6 or above, about 4.7 or above, about 4.8 or above, about 4.9 or above, about 5 or above, about 5.1 or above, about 5.2 or above, about 5.3 or above, about 4.5 to about 6.0, about 4.6 to about 5.8, about 4.7 to about 5.6, about 4.5 to about 5.5, about 4.6 to about 5.7, about 4.7 to about 5.8, about 5 to about 5.7, about 5.1 to about 5.6. It is to be understood that the pH of the solution may vary slightly upon storage, e.g. at accelerated or ambient conditions. Variance of ±0.05 to ±0.4 pH units, ±0.1 to ±0.3 pH units or ±0.05 to ±0.25 pH units may be noted upon storage.

In some embodiments provided herein, it is desirable to combine glacial acetic acid and sodium acetate trihydrate in the nasal preparation in proportions suitable to provide a stable pH (+/−0.2 pH units) of about 4.5 and above, about 4.6 or above, about 4.7 or above, about 4.8 or above, about 4.9 or above, about 5 or above, about 5.1 or above, about 5.2 or above, about 5.3 or above, about 4.5 to about 6.0, about 4.6 to about 5.8, about 4.7 to about 5.6, about 4.5 to about 5.5, about 4.6 to about 5.7, about 4.7 to about 5.8, about 5 to about 5.7, about 5.1 to about 5.6. Variance of ±0.05 to ±0.4 pH units, ±0.1 to ±0.3 pH units or ±0.05 to ±0.25 pH units may be noted upon storage.

In some embodiments, a suitable buffer will have at least one pKa in a range of about 4.2 to about 5.5, about 4.3 to about 5.3. about 4.4 to about 5.2, about 4.5 to about 5.1 or about 4.6 to about 5.0. In some embodiments, particularly desirable buffer will have a pKa in the range of about 4.7 to 4.8. In this regard, it is noted that acetic acid is reported to have a pKa of 4.75 and citric acid has three titratable groups with pKa values of 3.13, 4.76 and 6.40, of which 4.76 is within a range considered desirable for preparing compositions according to the present invention. In some embodiments, other buffers may be used if they have the appropriate pKa and buffering capacity.

A buffer used in the formulations according to the present invention should possess sufficient buffering capacity to maintain the pH of the solution within predetermined limits during storage. Buffering capacity of an acid/base buffer system may be influenced by various factors, among them being the total concentration of the buffer, which is the total concentration of the protonated (acid) form of the buffer and each complementary base. In the case of a citrate buffer, the total concentration of the buffer should be at least about 30 mM, or at least about 45 mM or at least about 55 mM. In the case of acetate buffer, the total concentration of acetic acid and free acetate ion should be greater than about 70 mM, greater than about 80 mM or greater than about 90 mM. In some embodiments, the buffering capacity of the selected buffer should be sufficient to maintain pH in the range of about ±0.1, 0.2 or 0.3 pH units upon storage at 25° C. to about 45° C. for a period of 2, 4, 6, 8, 10, 12, 16, 20, 24 or more weeks.

Some buffer systems that may be used in some embodiments of metoclopramide solutions as described herein include citric acid/phosphate, acetate, barbital, borate, Britton-Robinson, cacodylate, citrate, collidine, formate, maleate, McIlvaine, phosphate, Prideaux-Ward, succinate, citrate-phosphate-borate (Teorell-Stanhagen), veronal acetate, MES (2-(N-morpholino)ethanesulfonic acid), BIS-TRIS (bis(2-hydroxyethyl)iminotris(hydroxymethyl)methane), ADA (N-(2-acetamido)-2-iminodiacetic acid), ACES (N-(carbamoyl-methyl)-2-aminoethanesulfonaic acid), PIPES (piperazine-N,N'-bis(2-ethanesulfonic acid)), MOPSO (3-(N-morpholino)-2-hydroxypropanesulfonic acid), BIS-TRIS PROPANE (1,3-bis(tris(hydroxymethyl)methylamino)propane), BES (N,N-bis(2-hydroxyethyl)-2-aminoethanesulfonaic acid), MOPS (3-(N-morpholino)propanesulfonic acid), TES (N-tris(hydroxymethyl)methyl-2-aminoethanesulfonic acid), HEPES (N-(2-hydroxyethyl)piperazine-N'-(2-ethanesulfonic acid), DIPSO (3-(N,N-bis(2-hydroxyethyl)amino)-2-hydroxypropanesulfonic acid), MOBS (4-(N-morpholino)butanesulfonic acid), TAPSO (3-(N-tris(hydroxymethyl)methylamino)-2-hydroxy-propanesulfonic acid), tris(hydroxymethylaminomethane, HEPPSO(N-(2-hydroxyethyl)piperazine-N'-(2-hydroxypropanesulfonic acid), POPSO (piperazine-N,N'-bis(2-hydroxypropanesulfonic acid)), TEA (triethanolamine), EPPS(N-(2-hydroxyethyl)piperazine-N'-(3-propane-sulfonic acid), TRICINE (N-tris(hydroxymethyl)methylglycine), GLY-GLY (glycylglycine), BICINE (N,N-bis(2-hydroxyethyl)glycine), HEPBS (N-(2-hydroxyethyl)piperazine-N'-(4-butanesulfonic acid)), TAPS (N-tris(hydroxy-methyl)methyl-3-aminopropanesulfonic acid), or AMPD (2-amino-2-methyl-1,3-propanediol) buffer. In some embodiments, other pharmaceutically acceptable buffers may be used.

Antioxidants

In some embodiments, nasal compositions of metoclopramide may include one or more antioxidants suitable for administration to the nose or nasal cavity. In some embodiments, such antioxidants can include butylated hydroxyanisole, citric acid, citric acid monohydrate, sodium citrate dihydrate, or combinations of two or more thereof. In some particular embodiments, the antioxidant can include citric acid and/or sodium citrate.

Particular Excipients

In some embodiments, nasal compositions of metoclopramide may include one or more particular excipients suitable for administration to the nose or nasal cavity. In some embodiments, such excipients can include citric acid, sodium citrate, benzalkonium chloride, sorbitol, EDTA, or combinations of two or more thereof. In some particular embodiments, the excipients can include citric acid and/or sodium citrate. In some embodiments, the excipients can include benzalkonium chloride or a combination of benzalkonium chloride and citric acid and/or sodium citrate. In some embodiments, the excipients can include a combination of benzalkonium chloride and sorbitol, optionally with the addition of one or both of citric acid and sodium citrate.

Formulation of Nasal Compositions of Metoclopramide (Use for Production of a Medicament)

Nasal compositions of metoclopramide may be manufactured for administration as a medicament for administration to a patient for one of the indications described herein. Briefly, metoclopramide, buffer, benzalkonium chloride and optionally other ingredients (such as sodium chloride or other osmolarity-regulating agent, sorbitol or other sweetener, flavoring agent, etc.) may be made up to some volume less than the target final volume of the solution. The ingredients may then be mixed until all the ingredients are dissolved. The pH then may be adjusted, if necessary, by addition of a suitable acid or base, such as HCl, NaOH, or the complementary acid or base of the buffer. Once the desired pH has been obtained, the solution may then be brought up to full volume with water. The resulting solution may then be packaged in a suitable container for shipping and distribution. In some embodiments, the suitable container includes a nasal pump as described in more detail below. In other embodiments, the suitable container may be a vial, such as an amber glass vial, which may be a glass ampule, a glass bottle topped with an inert rubber septum and crimp cap top, or other suitable pharmaceutical vial.

Manufacture

Some embodiments described herein provide, as a manufacture, a combination of a stable, clear and/or colorless solution of metoclopramide and a means for intranasal administration of the metoclopramide solution. In some embodiments, the manufacture comprises one of the metoclopramide solutions described herein and an intranasal delivery device comprising a reservoir, in which the metoclopramide solution is contained, a pump in fluid communication with the reservoir and a nozzle in fluid communication with the pump. In use, the pump is actuated, drawing an amount of the metoclopramide solution from the reservoir and expelling the solution out of the nozzle as an aerosolized spray. Suitable nasal administration devices are commercially available. Among the suppliers of nasal administration devices that may be combined with a stable, substantially clear and/or substantially colorless metoclopramide solution according to the present invention, there may be mentioned Valois of America, Congers, N.Y., and Pfeiffer of America, Princeton, N.J. In some embodiments, the intranasal delivery device is partially or completely opaque, in order to protect the contents of the device from exposure to ambient light.

Stability of Nasal Compositions of Metoclopramide

Compositions described herein comprise metoclopramide, or a pharmaceutically acceptable salt thereof, in a stable composition. In some embodiments described herein, stable metoclopramide solutions are solutions containing metoclopramide characterized by color stability or clarity of the solution. In some embodiments, color stability refers to the tendency of a formulated solution to maintain the same color, or absence of color, upon storage for a predetermined period of time as it had when originally formulated. In some embodiments, stability refers to the tendency of a formulated solution to maintain the same clarity upon storage for a predetermined period of time as it had when originally formulated. In some embodiments, stability refers to the tendency of a formulated solution to resist degradation of one or more ingredients, and in particular metoclopramide, during storage. In some embodiments, such compositions are stable for a period of at least about 1 month, at least about 2 months, at least about 3 months, at least about 4 months, at least about 5 months, at least about 6 months, at least about 9 months, at least about 12 months, at least about 15 months, at least about 18 months, at least about 21 months or at least about 24 months at temperatures in the range of about 5° C. to about 25° C. In some embodiments, long-term storage at 5°-25° C. may be simulated under accelerated conditions, e.g. at a temperature in the range of about 35° C. to about 60° C., particularly in a range of about 35° C. to about 45° C., e.g. about 40° C. Thus, in some embodiments, the nasal compositions of metoclopramide provided herein are stable upon storage under accelerated conditions, e.g. at about 25° C. to about 60°, especially at about 30° C. to about 50° C., about 35° C. to about 45° C. or about 40° C. for at least about 1 week, at least about 2 weeks, at least about 3 weeks, at least about 4 weeks, at least about 5 weeks, at least about 6 weeks, at least about 9 weeks, at least about 12 weeks, at least about 15 weeks, at least about 18 weeks, at least about 21 weeks or at least about 24 weeks.

Stability may be determined by methods known in the art, such as those dictated by the United States Pharmacopoeia (USP). In particular, USP 26, pages 500-502, and 2138-2140 (incorporated herein by reference) provide general procedures for preparing standard colored solutions for color determination and for determining the color or achromicity of a solution. Thus, the person skilled in the art will know how to prepare standard solutions and compare the color of a composition of the invention against standard solutions. 32 USP <631>, pages 238-239 (incorporated herein by reference) provide standardized methods for measuring the stability of metoclopramide in injectable and oral solutions of metoclopramide. The person skilled in the art would thus know how to test the stability of metoclopramide compositions. Color standards can also include standards A, B, C, D and/or E described in 32 USP <631>. In some embodiments, another color standard that may be useful for determining the stability of nasal metoclopramide solutions is the a 50:50 dilution of standard C with distilled water, wherein C is as described in 32 USP <631>. The 50:50 dilution of C with distilled water is also referred to herein at 0.5 C, and can be prepared by combining 1 mL Cobaltous Chloride CS, 6 mL Ferric Chloride CS, 1 mL Cupric Sulfate CS, and q.s. to 50 mL with distilled water to produce standard C and then diluting C to 0.5 C by combining 1 part C with 1 part distilled water. A solution that is lighter than 0.5 C is considered to be substantially clear as the term is used herein. The Cobaltous Chloride CS, Ferric Chloride CS and Cupric Sulfate CS are colorometric solutions are commercially available; they may also be prepared according to 32 USP under Colorimetric Solutions (CS) in the section Reagents, Indicators, and Solutions, which is incorporated by reference herein in its entirety. In some other preferred embodiments, the color reference standard is "E" from 32 USP <631>. The standard matching solution "E" is prepared by combining 4.0 mL of cobaltous chloride colorometric solution (USP CS), 12.0 mL of ferric chloride colorometric solution (USP CS), and 3.0 mL of cupric sulfate solution (USP CS) into a 50 mL volumetric flask and making the flask up to 50 mL with deionized water. Color determination is conducted by pipetting 5.0 mL of standard matching solution into a 20 mL scintillation vial (about 15 mm height), pipetting 5.0 mL of sample solution into a separate 20 mL scintillation vial (about 15 mm height) and comparing the color of the two solutions under diffused day light against a vertical white background. In some embodiments, a sample whose color is clear, lighter than the standard or the same color as the standard is considered "substantially free of color", "substantially clear" or "stable" as described herein. Objectivity may be ensured by having the color of a test solution evaluated against the standard solution by more than one person.

In some embodiments, the metoclopramide compositions described herein are colorless when formulated and remain colorless for a period of at least about 2 weeks, about 1 month, at least about 2 months, at least about 3 months, at least about 4 months, at least about 5 months, at least about 6 months, at least about 9 months, at least about 12 months, at least about 15 months, at least about 18 months, at least about 21 months or at least about 24 months at temperatures in the range of about 5° C. to about 25° C. In some embodiments, long-term storage at 5°-25° C. may be simulated under accelerated conditions, e.g. at a temperature in the range of about 35° C. to about 60° C., particularly in a range of about 35° C. to about 45° C., e.g. about 40° C. Thus, in some embodiments, the nasal compositions of metoclopramide provided herein are colorless when formulated and remain colorless upon storage under accelerated conditions, e.g. at about 25° C. to about 60°, especially at about 30° C. to about 50° C., about 35° C. to about 45° C. or about 40° C. for at least about 1 week, at least about 2 weeks, at least about 3 weeks, at least about 4 weeks, at least about 5 weeks, at least about 6 weeks, at least about 9 weeks, at least about 12 weeks, at least about 15 weeks, at least about 18 weeks, at least about 21 weeks or at least about 24 weeks.

Methods of Treatment with Nasally Administered Metoclopramide

Pharmaceutical formulations described herein may be employed in methods for the treatment of one or more disease states treatable with metoclopramide. In some embodiments, the pharmaceutical compositions can be used to treat a patient for gastroparesis, emesis, delayed emesis or nausea, or any combination of two or more of these indications.

In some embodiments provided herein, gastroparesis is treated by intranasal instillation of a pharmaceutically active amount of a metoclopramide solution described herein. Metoclopramide nasal dosage form at a therapeutic dosage level of between about 20 mg/day to about 160 mg/day for about 1 to about 8 weeks, about 5 weeks to about 8 weeks, or about 1, 2, 3, 4, 5, 6, 7, 8 or more weeks.

In some embodiments, a method for treating gastroparesis comprises intranasally administering a nasal metoclopramide composition as described herein at a metoclopramide dosage of about 40 mg/day to about 160 mg/day in 3 to 4 smaller dosages at equally spaced intervals within 24 hours for about 1 to about 8 weeks, about 2 to 6 weeks or about 1, 2, 3, 4, 5, 6, 7, 8 or more weeks. Daily dosing may be varied according to the particular characteristics of the various patients. A clinical practitioner or pharmacist will be able to modify the administered dosage and dosing regimen in order to treat the particular patient. In some embodiments, from 1 to about 8, from 1 to 4 or 1, 2, 3, 4, 5, 6, 7, 8 or more doses may be administered in a day, depending upon the needs and tolerance of the patient. In some embodiments, a therapeutic dosage level of metoclopramide will be from about 20 mg/day to about 160 mg/day, about 30 mg/day, about 35 mg/day, about 40 mg/day, about 45 mg/day, about 55 mg/day, about 60 mg/day, about 65 mg/day, about 70 mg/day, about 75 mg/day, about 80 mg/day, about 85 mg/day, about 90 mg/day, about 95 mg/day, about 100 mg/day, about 105 mg/day, about 110 mg/day, about 115 mg/day, about 120 mg/day, about 125 mg/day, about 130 mg/day, about 135 mg/day, about 140 mg/day, about 145 mg/day, about 150 mg/day, about 155 mg/day, about 160 mg/day. These daily dosages may be broken into smaller doses, which may be spread over different parts of a day. Smaller doses may be about 5 to about 30 mg, e.g. about 5 mg, about 10 mg, about 15 mg, about 20 mg, about 25 mg or about 30 mg. Administration of about 3-4 smaller dosages at equally spaced intervals within a 24-hour period or about 1-8 weeks is contemplated. Administration may be prescribed before meals, assuming 2 to 4 meals per day, and before bedtime.

In some embodiments, the method comprises treatment of gastroparesis of varying etiology, including gastroparesis arising out, associated with or caused by diabetes (including type 1 and type 2), postviral syndromes, anorexia nervosa, surgery on the stomach or vagus nerve, medications, such as anticholinergic and narcotic medications, which tend to suppress intestinal and gastroesophageal contractions, gastroesophageal reflux disease, smooth muscle disorders (e.g. amyloidosis and scleroderma), nervous system diseases (including abdominal migraine and Parkinson's disease), and/or metabolic disorders (including hypothyroidism).

In some embodiments, the gastroparesis is of diabetic origin, including type 1 and type 2 diabetes and treatment comprises intranasally administering a nasal composition of metoclopramide as described herein in a nasal spray dosage form and at a therapeutic dosage level of between about 40 mg/day to about 160 mg/day in 3 to 4 smaller dosages at equally spaced intervals within 24 hours for about 1 to about 8 weeks, for about 2 weeks to about 8 weeks or for 1, 2, 3, 4, 5, 6, 7, 8 or more weeks.

In some embodiments, treatment comprises intranasally administering a nasal composition of metoclopramide as described here at a therapeutic dosage level of between about 40 mg/day to about 80 mg/day in 3 to 4 smaller dosages at equally spaced intervals within 24 hours for about 1 to about 8 weeks, for about 2 weeks to about 8 weeks or for 1, 2, 3, 4, 5, 6, 7, 8 or more weeks.

In some embodiments provided herein, emesis, delayed emesis or nausea is treated by intranasal instillation of a pharmaceutically active amount of a metoclopramide solution described herein. Metoclopramide nasal dosage form at a therapeutic dosage level of between about 20 mg/day to about 160 mg/day for about 1 to about 8 weeks, about 5 weeks to about 8 weeks, or about 1, 2, 3, 4, 5, 6, 7, 8 or more weeks.

In some embodiments, a method for treating, emesis, delayed emesis or nausea comprises intranasally administering a nasal metoclopramide composition as described herein at a metoclopramide dosage of about 40 mg/day to about 160 mg/day in 3 to 4 smaller dosages at equally spaced intervals within 24 hours for about 1 to about 8 weeks, about 2 to 6 weeks or about 1, 2, 3, 4, 5, 6, 7, 8 or more weeks. Daily dosing may be varied according to the particular characteristics of the various patients. A clinical practitioner or pharmacist will be able to modify the administered dosage and dosing regimen in order to treat the particular patient. In some embodiments, from 1 to about 8, from 1 to 4 or 1, 2, 3, 4, 5, 6, 7, 8 or more doses may be administered in a day, depending upon the needs and tolerance of the patient. In some embodiments, a therapeutic dosage level of metoclopramide will be from about 20 mg/day to about 160 mg/day, about 30 mg/day, about 35 mg/day, about 40 mg/day, about 45 mg/day, about 55 mg/day, about 60 mg/day, about 65 mg/day, about 70 mg/day, about 75 mg/day, about 80 mg/day, about 85 mg/day, about 90 mg/day, about 95 mg/day, about 100 mg/day, about 105 mg/day, about 110 mg/day, about 115 mg/day, about 120 mg/day, about 125 mg/day, about 130 mg/day, about 135 mg/day, about 140 mg/day, about 145 mg/day, about 150 mg/day, about 155 mg/day, about 160 mg/day. These daily dosages may be broken into smaller doses, which may be spread over different parts of a day. Smaller doses may be about 5 to about 30 mg, e.g. about 5 mg, about 10 mg, about 15 mg, about 20 mg, about 25 mg or about 30 mg. Administration of about 3-4 smaller dosages at equally spaced intervals within a 24-hour period or about 1-8 weeks is contemplated. Administration may be prescribed before meals, assuming 2 to 4 meals per day, and before bedtime.

In some embodiments, a pharmaceutical composition administered for the treatment of one or more clinical indications as described herein consists of: metoclopramide (e.g. as metoclopramide HCl), citric acid (e.g. as the monohydrate), sodium citrate (e.g. as the dihydrate), benzalkonium chloride (e.g. as a 50% solution, N.F.), sorbitol (e.g. as a solution, such as a 70% solution USP), edetate disodium, sodium chloride and purified water. In some embodiments, a pharmaceutical composition administered for the treatment of one or more clinical indications described herein consists of: metoclopramide (e.g. as metoclopramide HCl), citric acid (e.g. as the monohydrate), sodium citrate (e.g. as the dihydrate), benzalkonium chloride (e.g. as a 50% solution, N.F.), edetate disodium, sodium chloride and purified water. In some embodiments, a pharmaceutical composition administered for the treatment of one or more clinical indications described herein consists of: metoclopramide (e.g. as metoclopramide HCl), citric acid (e.g. as the monohydrate), sodium citrate (e.g. as the dihydrate), benzalkonium chloride (e.g. as a 50% solution, N.F.), sodium chloride and purified water.

In some embodiments, a pharmaceutical composition administered for the treatment of one or more clinical indications as described herein consists of: metoclopramide (e.g. as metoclopramide HCl, 15-30% w/v, 20-25% w/v or 22-24% w/v), citric acid (e.g. as the monohydrate, 0.2-0.5% w/v, 0.25-0.4% w/v or 0.3-0.35% w/v), sodium citrate (e.g. as the dihydrate, 1.0-1.8% w/v, 1.2-1.6% w/v or about 1.3-1.5% w/v), benzalkonium chloride (e.g. as a 50% solution, N.F., about 0.01-0.05% w/v, about 0.02-0.04% w/v or about 0.02-0.03% w/v), sorbitol (e.g. as a solution, such as a 70% solution USP, about 1-5% w/v, about 2-4% w/v or about 2.5-3.5% w/v), edetate disodium, sodium chloride and purified water. In some embodiments, a pharmaceutical composition administered for the treatment of one or more clinical indications described herein consists of: metoclopramide (e.g. as metoclopramide HCl, 15-30% w/v, 20-25% w/v or 22-24% w/v), citric acid (e.g. as the monohydrate, 0.2-0.5% w/v, 0.25-0.4% w/v or 0.3-0.35% w/v), sodium citrate (e.g. as the dihydrate, 1.0-1.8% w/v, 1.2-1.6% w/v or about 1.3-1.5% w/v), benzalkonium chloride (e.g. as a 50% solution, N.F., about 0.01-0.05% w/v, about 0.02-0.04% w/v or about 0.02-0.03% w/v), edetate disodium, sodium chloride and purified water. In some embodiments, a pharmaceutical composition administered for the treatment of one or more clinical indications described herein consists of: metoclopramide (e.g. as metoclopramide HCl, 15-30% w/v, 20-25% w/v or 22-24% w/v), citric acid (e.g. as the monohydrate, 0.2-0.5% w/v, 0.25-0.4% w/v or 0.3-0.35% w/v), sodium citrate (e.g. as the dihydrate, 1.0-1.8% w/v, 1.2-1.6% w/v or about 1.3-1.5% w/v), benzalkonium chloride (e.g. as a 50% solution, N.F., about 0.01-0.05% w/v, about 0.02-0.04% w/v or about 0.02-0.03% w/v), sodium chloride and purified water. The amount of edetate disodium, if present, may be between about 0.01 and 0.2% w/v, e.g. about 0.05-0.15% w/v or about 0.1% w/v. The amount of sodium chloride may be adjusted to attain a desirable osmolality for the solution. Suitable concentrations of sodium chloride include about 0.1-2.0% w/v, 0.2-1.5% w/v and 0.5-1.0% w/v. A suitable acid or base may be added to attain the desired pH. Such acids and bases include HCl and NaOH. A suitable pH may be in the range of about pH 4.5-6.0, e.g. about 4.7-5.7 or about 4.8-5.6, about 4.7, about 4.8, about 4.9, about 5.0, about 5.1, about 5.2, about 5.3, about 5.4, about 5.5, about 5.6 or about 5.7.

In some embodiments, a pharmaceutical composition administered for the treatment of one or more clinical indications as described herein consists of: metoclopramide (e.g. as metoclopramide HCl), acetic acid (e.g. as glacial acetic acid), sodium acetate (e.g. as the trihydrate), benzalkonium chloride (e.g. as a 50% solution, N.F.), sorbitol (e.g. as a solution, such as a 70% solution USP), edetate disodium, sodium chloride and purified water. In some embodiments, a pharmaceutical composition administered for the treatment of one or more clinical indications described herein consists of: metoclopramide (e.g. as metoclopramide HCl), acetic acid (e.g. as glacial acetic acid), sodium acetate (e.g. as the trihydrate), benzalkonium chloride (e.g. as a 50% solution, N.F.), edetate disodium, sodium chloride and purified water. In some embodiments, a pharmaceutical composition administered for the treatment of one or more clinical indications described herein consists of: metoclopramide (e.g. as metoclopramide HCl), acetic acid (e.g. as glacial acetic acid), sodium acetate (e.g. as the trihydrate), benzalkonium chloride (e.g. as a 50% solution, N.F.), sodium chloride and purified water.

In some embodiments, a pharmaceutical composition administered for the treatment of one or more clinical indications as described herein consists of: metoclopramide (e.g. as metoclopramide HCl, 15-30% w/v, 20-25% w/v or 22-24% w/v), acetic acid (e.g. as glacial acetic 0.02-0.10% w/v, 0.03-0.08% w/v or 0.04-0.07% w/v), sodium acetate (e.g. as the trihydrate, 0.4-1.0% w/v, 0.5-0.9% w/v or 0.4-0.8% w/v), benzalkonium chloride (e.g. as a 50% solution, N.F., about 0.01-0.05% w/v, about 0.02-0.04% w/v or about 0.02-0.03% w/v), sorbitol (e.g. as a solution, such as a 70% solution USP, about 2-10% w/v, about 4-8% w/v or about 5-7% w/v), edetate disodium, sodium chloride and purified water. In some embodiments, a pharmaceutical composition administered for the treatment of one or more clinical indications described herein consists of: metoclopramide (e.g. as metoclopramide HCl, 15-30% w/v, 20-25% w/v or 22-24% w/v), acetic acid (e.g. as glacial acetic 0.02-0.10% w/v, 0.03-0.08% w/v or 0.04-0.07% w/v), sodium acetate (e.g. as the trihydrate, 0.4-1.0% w/v, 0.5-0.9% w/v or 0.4-0.8% w/v), benzalkonium chloride (e.g. as a 50% solution, N.F., about 0.01-0.05% w/v, about 0.02-0.04% w/v or about 0.02-0.03% w/v), edetate disodium, sodium chloride and purified water. In some embodiments, a pharmaceutical composition administered for the treatment of one or more clinical indications described herein consists of: metoclopramide (e.g. as metoclopramide HCl, 15-30% w/v, 20-25% w/v or 22-24% w/v), acetic acid (e.g. as glacial acetic 0.02-0.10% w/v, 0.03-0.08% w/v or 0.04-0.07% w/v), sodium acetate (e.g. as the trihydrate, 0.4-1.0% w/v, 0.5-0.9% w/v or 0.4-0.8% w/v), benzalkonium chloride (e.g. as a 50% solution, N.F., about 0.01-0.05% w/v, about 0.02-0.04% w/v or about 0.02-0.03% w/v), sodium chloride and purified water. The amount of edetate disodium, if present, may be between about 0.01 and 0.2% w/v, e.g. about 0.05-0.15% w/v or about 0.1% w/v. The amount of sodium chloride may be adjusted to attain a desirable osmolality for the solution. Suitable concentrations of sodium chloride include about 0.1-2.0% w/v, 0.2-1.5% w/v and 0.5-1.0% w/v. A suitable acid or base may be added to attain the desired pH. Such acids and bases include HCl and NaOH. A suitable pH may be in the range of about pH 4.5-6.0, e.g. about 4.7-5.7 or about 4.8-5.6, about 4.7, about 4.8, about 4.9, about 5.0, about 5.1, about 5.2, about 5.3, about 5.4, about 5.5, about 5.6 or about 5.7.

The nasal metoclopramide compositions described herein may be administered a patient as 1 spray in a single nostril, four times a day (1 spray QID for about 1, 2, 3, 4, 5, 6, 7, or 8 weeks), or 1 spray per nostril in both nostrils four times a day (2 sprays QID for about 1, 2, 3, 4, 5, 6, 7, or 8 weeks). Those skilled in the art (e.g. clinicians and pharmacists) will recognize that a systemic, therapeutically effective amount of metoclopramide for treating gastroparesis, emesis, delayed emesis, nausea or a combination of two or more thereof, will vary with the age, size, weight and general physical condition of the patient, as well as the severity of the disease. Frequency of administration will likewise vary with the formulation of nasal metoclopramide (i.e., the concentration of metoclopramide, whether it is in the form of sustained release, etc.) and can be adjusted so that any suitable number of doses per day may be used.

The methods of treatment provided herein can also include co-administration of one or more additional therapeutic agents along with the metoclopramide nasal formulations described herein. The additional therapeutic agents administered concurrently with metoclopramide or at separate time intervals. In some embodiments, one or more other drugs may be incorporated into the metoclopramide nasal formulation. Additional therapeutic agents may include pain relievers, insulin and other drugs useful in the management of diabetes, steroids, especially steroids that prevent nasal irritation, and antidepressants.

Various techniques may be used to assess the severity of the gastroparesis and gastric emptying, and these will be well-known to those of skill in the art. Such techniques include questioning the patient regarding symptoms of gastroparesis. Techniques like radioscintigraphy, ultrasonography, and x-rays employing radiopaque markers such as barium, may be employed.

As the weight of the patient may affect the dosage to be administered, the person skilled in the art will know to vary or titrate the dose in order to obtain an optimal effect in relation to the dose tolerated by the patient. For example, a dose of between about 0.1 mg/kg to about 2.5 mg/kg may be administered to a patient having gastroparesis. Exemplary dosages can be about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg. In some embodiments, a nasal dosage is between about 0.06 to about 1.2 mg/kg of body weight. In some embodiments, the nasal dosages are about 0.06 mg/kg, 0.08 mg/kg, 1.0 mg/kg, 1.2 mg/kg and 1.4 mg/kg.

The aforementioned dosages for the treatment and control of gastroparesis may be administered before meals and/or before bed time.

EXAMPLES

Comparative Example 1

Discoloration of Metoclopramide Solutions

In order to evaluate the stability of metoclopramide solutions, various compositions comprising metoclopramide are prepared according to the following Table CX1-1. These compositions are set up on stability under accelerated conditions (40° C./75% RH) for 1, 2, 4, or 8 weeks.

TABLE CX1-1

| Sample | CX 1, CX 2 | CX 3 | CX 4 | CX 5 | CX 6 | CX 7 | CX 8 | CX 9 | CX 10 |
|---|---|---|---|---|---|---|---|---|---|
| Metoclopramide | 400 mg/mL & 200 mg/mL | 200 mg/mL | 200 mg/mL | 200 mg/mL | 100 mg/mL | 100 mg/mL | 100 mg/mL | 100 mg/mL | 200 mg/mL |
| Acetic Acid (mg/mL) | 3.20 | — | 3.20 | 3.20 | 3.20 | 3.20 | 3.20 | 3.20 | 3.20 |
| Acetic Acid (mmol/mL) | 0.0533 | — | 0.0533 | 0.0533 | 0.0533 | 0.0533 | 0.0533 | 0.0533 | 0.0533 |
| Sodium Acetate (mg/mL) | 0.77 | — | 0.77 | 0.77 | 0.77 | 0.77 | 0.77 | 0.77 | 0.77 |
| Sodium Acetate (mmol/mL) | 0.0094 | — | 0.0094 | 0.0094 | 0.0094 | 0.0094 | 0.0094 | 0.0094 | 0.0094 |
| Citric Acid (mg/mL) | — | 0.16 | — | — | — | — | — | — | — |
| Citric Acid (mmol/mL) | — | 0.0020 | — | — | — | — | — | — | — |
| Sodium Citrate (mg/mL) | — | 0.50 | — | — | — | — | — | — | — |
| Sodium Citrate (mmol/mL) | — | 0.0026 | — | — | — | — | — | — | — |
| NaCl | 8.00 | — | 8.00 | 8.00 | — | — | — | — | — |
| Sorbitol | 64.3 | — | 64.2 | 64.2 | — | — | — | — | — |
| EDTA | — | — | — | 1.0 | — | — | — | — | — |
| BAC | — | 0.40 | — | — | — | — | — | — | — |
| Benzyl-OH | 15.0 | — | 15.0 | 15.0 | — | — | — | — | — |
| pH Calc. | 4.00 | 4.89 | 4.00 | 4.00 | 4.00 | 4.00 | 4.00 | 4.00 | 4.00 |
| Total Buffer (mmol/mL) | 0.063 | 0.005 | 0.063 | 0.063 | 0.063 | 0.063 | 0.063 | 0.063 | 0.063 |
| pH Calc. | 4.00 | 4.89 | 4.00 | 4.00 | 4.00 | 4.00 | 4.00 | 4.00 | 4.00 |
| Total Buffer (mmol/mL) | 0.063 | 0.005 | 0.063 | 0.063 | 0.063 | 0.063 | 0.063 | 0.063 | 0.063 |

Each of the solutions become substantially colored upon storage under the conditions outlined above, the discoloration tending from a very light yellow to a darker yellow-brown.

Example 1

Formulation of Nasally Administrable Metoclopramide Compositions

Several metoclopramide solutions were prepared in order to evaluate the stability, clarity and/or tendency to become colored on storage of various formulations. The composition of these solutions are set forth in the following Table 1-1, where the compositions are numbered 1-10. These compositions were filled into two different samples of pumps (Valois) attached to amber glass vials and were stored at 40° C./75% RH and were observed at the end of 2, 4 and 8 weeks. The results of these studies are shown in Table 1-1.

TABLE 1-1

Composition of formulations 1-10

| Ingredient | Formulation Number | | | | | | | | | |
|---|---|---|---|---|---|---|---|---|---|---|
| | 1 | 2 | 3 | 4 | 5 | 6 | 7 | 8 | 9 | 10 |
| Metoclopramide HCL USP mg/mL | 23.64 | 23.64 | 23.64 | 23.64 | 23.64 | 23.64 | 23.64 | 23.64 | 23.64 | 23.64 |
| Acetic Acid (mg/mL) | 0.57 | — | — | — | 0.57 | 0.57 | 0.57 | 0.57 | 0.57 | — |
| Acetic Acid (mmol/mL) | 0.0095 | — | — | — | 0.0095 | 0.0095 | 0.0095 | 0.0095 | 0.0095 | — |

TABLE 1-1-continued

Composition of formulations 1-10

| Ingredient | Formulation Number | | | | | | | | | |
|---|---|---|---|---|---|---|---|---|---|---|
| | 1 | 2 | 3 | 4 | 5 | 6 | 7 | 8 | 9 | 10 |
| Sodium Acetate (mg/mL) | 7.28 | — | — | — | 7.28 | 7.28 | 7.28 | 7.28 | 7.28 | — |
| Sodium Acetate (mmol/mL) | 0.0535 | — | — | — | 0.0535 | 0.0535 | 0.0535 | 0.0535 | 0.0535 | — |
| Citric Acid (mg/mL) | — | 1.00 | 1.00 | 1.00 | — | — | — | — | — | 1.00 |
| Citric Acid (mmol/mL) | — | 0.0048 | 0.0048 | 0.0048 | — | — | — | — | — | 0.0048 |
| Sodium Citrate (mg/mL) | — | 4.40 | 4.40 | 4.40 | — | — | — | — | — | 4.40 |
| Sodium Citrate (mmol/mL) | — | 0.0150 | 0.0150 | 0.0150 | — | — | — | — | — | 0.0150 |
| NaCl | 8.00 | 8.00 | — | — | — | — | — | — | — | — |
| Sorbitol | 3.0 | 3.0 | — | — | — | 3.0 | — | 3.0 | — | — |
| EDTA | 1.0 | 1.0 | 1.0 | — | — | 1.0 | 1.0 | 1.0 | 1.0 | 1.0 |
| BAC | 0.25 | 0.25 | 0.25 | 0.25 | 0.25 | — | — | 0.25 | 0.25 | — |
| Menthol | 0.80 | — | — | — | 0.80 | — | — | — | — | — |
| Benzyl-OH | — | — | — | — | — | 7.5 | 7.5 | — | — | 7.5 |
| Methocel | — | — | — | — | — | — | — | — | — | — |
| mOsm | 1233 | 1286 | 693 | 693 | 820 | 1067 | 787 | 1042 | 759 | 755 |
| pH Initial | 5.36 | 5.34 | 5.41 | 5.40 | 5.37 | 5.62 | 5.64 | 5.58 | 5.62 | 5.42 |
| pH Week 2 | 5.20 | 5.16 | 5.24 | 5.14 | 5.22 | 5.40 | 5.58 | 5.38 | 5.44 | 5.12 |
| ΔpH | −0.16 | −0.18 | −0.17 | −0.26 | −0.15 | −0.22 | −0.06 | −0.20 | −0.18 | −0.30 |
| % ΔpH | −2.99 | −3.37 | −3.14 | −4.81 | −2.79 | −3.91 | −1.06 | −3.58 | −3.20 | −5.54 |
| Total Buffer (mmol/mL) | 0.063 | 0.020 | 0.020 | 0.020 | 0.063 | 0.063 | 0.063 | 0.063 | 0.063 | 0.020 |

Tables 1-2A and 1-2B set forth results of stability studies performed in Pfeiffer pumps at 40° C./75% RH at 4 and 8 week time points. Table 1-2A contains the data for Sample 1 (first set of pumps), and Table 1-2B contains the data for Sample 2 (second set of pumps) from this study.

TABLE 1-2A (Sample 1)

| Composition | Color: Week 4 | Color: Week 8 |
|---|---|---|
| 1 | ND | ND |
| 2 | ND | ND |
| 3 | ND | ND |
| 4 | ND | ND |
| 5 | ND | VLBS |
| 6 | VLBS | LBS |
| 7 | VLBS | LBS |
| 8 | ND | ND |
| 9 | ND | ND |
| 10 | VLBS | VLBS |

TABLE 1-2B (Sample 2)

| Formulation | Color: Week 4 | Color: Week 8 |
|---|---|---|
| 1 | ND | ND |
| 2 | ND | ND |
| 3 | ND | ND |
| 4 | ND | ND |
| 5 | ND | ND |
| 6 | VLBS | VLBS |
| 7 | VLBS | VLBS |
| 8 | ND | ND |
| 9 | ND | ND |
| 10 | VLBS | VLBS |

Key for Tables 1-2A, 1-2B:
ND = Substantially Free of Color Brown
BS = Solution
LBS = Light Brown Solution
VLBS = Very Light Brown Solution Tables 1-3A and 1-3B show the results of a stability study carried out in Valois pumps at 40° C./75% RH, with observations taken at 2, 4 and 8 week time points. Table 1-3A contains the data for Sample 1 and Table 1-3B contains the data for Sample 2 from this study.

TABLE 1-3A

| Composition | Color: Week 2 | Color: Week 4 | Color: Week 8 |
|---|---|---|---|
| 1 | ND | ND | ND |
| 2 | ND | ND | ND |
| 3 | ND | ND | ND |
| 4 | ND | ND | ND |
| 5 | ND | ND | ND |
| 6 | VLBS | VLBS | VLBS |
| 7 | VLBS | VLBS | VLBS |
| 8 | ND | ND | ND |
| 9 | ND | ND | ND |
| 10 | VLBS | VLBS | VLBS |

TABLE 1-3B

| Formulation | Week 2 | Week 4 | Week 8 |
|---|---|---|---|
| 1 | ND | ND | ND |
| 2 | ND | ND | ND |
| 3 | ND | ND | ND |
| 4 | ND | ND | ND |
| 5 | ND | ND | ND |
| 6 | VLBS | VLBS | VLBS |
| 7 | VLBS | VLBS | VLBS |
| 8 | ND | ND | ND |
| 9 | ND | ND | ND |
| 10 | VLBS | VLBS | VLBS |

Key for Tables 1-3A, 1-3B
ND = Substantially Free of Color Brown
BS = Solution
LBS = Light Brown Solution
VLBS = Very Light Brown Solution As can be seen in Tables 1-2A, 1-2B, 1-3A and 1-3B, compositions 1-5 and 8-9 remained substantially free of color through 8 weeks under accelerated conditions of 40° C. and 75% relative humidity. In contrast, compositions 6, 7 and 10 all became discolored to some extent; and such discoloration was observable after only two weeks under the accelerated conditions.

Example 2

Stability Studies of Nasal Metoclopramide Compositions

Introduction and Background

An analytical testing method was developed to quantify discoloration of five metoclopramide hydrochloride nasal spray solutions employing guidelines in the United States Pharmacopeia (USP). See, 32 USP <631>, <1061> and <851>.

Preparation of Test Samples

Test samples were prepared having the formulations set forth in Table 2-1, below, according to the following procedure. Water was purged with nitrogen gas for about 20 minutes and a gentle nitrogen sparge was maintained during preparation of the solution. About 50-60% of the required amount of purified water was charged into a glass beaker containing a Teflon® stir bar and wrapped with aluminum foil. Benzyl alcohol and benzalkonium chloride were then added to the water and mixed. (In formulations F-1 and F-22, menthol was first added to benzyl alcohol and mixed until visually dissolved; then the benzyl alcohol, menthol solution was added to the water.) Edetate disodium was added to the solution and mixed until dissolved. Buffering ingredients (acetic acid/sodium acetate or citric acid/sodium citrate) were added in sequence and mixed until dissolved. Metoclopramide hydrochloride was then added slowly to the solution and mixed until dissolved. Sorbitol was then added and mixed until dissolved. The pH was then measured and recorded. The pH was adjusted, if necessary, and the amount of buffer agent added was recorded. The solution in the mixing tank was then brought up to its final volume by adding previously-purged purified water. The resulting solution was then filtered through a 10 μm cartridge filter. Filtered solution was then dispensed into clear glass vials, which were wrapped with aluminum foil. Representative samples were tested for potency (metoclopramide concentration) by a reverse phase high performance liquid chromatography (RP-HPLC) method that had been previously developed and validated.

TABLE 2-1

Composition of Five Metoclopramide Formulations

| | Formulation (% w/v) | | | | |
|---|---|---|---|---|---|
| Ingredient | F-1 | F-22 | F-43 | F-60 | F-P |
| Metoclopramide HCl, USP | 23.64* | 23.64* | 23.64* | 23.64* | 23.64* |
| Glacial Acetic Acid, USP | 0.32 | 0.057 | 0.057 | — | — |
| Sodium Acetate trihydrate, USP | 0.128 | 0.728 | 0.728 | — | — |
| Citric Acid monohydrate, USP | — | — | — | 0.10 | 0.10 |
| Sodium Citrate dihydrate, USP | — | — | — | 0.44 | 0.44 |
| Benzyl Alcohol, NF | 1.5 | 1.5 | — | 0.75 | — |
| Benzalkonium Chloride Solution 50%, NF | — | — | 0.025 | — | 0.025 |
| Sodium Chloride, USP | 0.8 | 0.8 | — | — | — |
| Edetate Disodium, dehydrate, USP | 0.1 | 0.1 | 0.1 | 0.1 | 0.1 |
| Sorbitol Solution (70%), USP | 6.424 | 6.424 | 3.00 | — | 3.00 |
| Menthol Crystals, USP | 0.08 | 0.08 | — | — | — |
| Purified Water, USP | QS | QS | QS | QS | QS |
| pH | 3.90 | 5.5 ± 0.2 | 5.5 ± 0.2 | 5.5 ± 0.2 | 5.5 ± 0.2 |

Analytical Method

Optical density (OD) was calculated according to the following formula:

$$\% \; OD = \frac{\text{Absorbance of Sample} \times 100\%}{\text{Absorbance of Standard}}$$

wherein:

Absorbance of Standard is the absorbance at 450 nm of 0.0005 M iodine in water; and Absorbance of Sample is the absorbance at 450 nm of a metoclopramide sample as described herein.

The OD was measured at 450 nm on the first day and after 1, 2, 4, and 8 weeks of storage under normal conditions (25° C./60% RH) and accelerated conditions (40° C./75% RH).

Five formulations containing about 200 mg/mL metoclopramide as free base were assayed for drug potency and optical density. These data are presented in Table 2-2. Each freshly prepared formulation demonstrated a pale, light brownish color. The initial optical density of each formulation was determined to be about 5-6%, as calibrated with respect to a 0.0005 M iodine solution at 450 nm.

TABLE 2-2

Potency assays and optical densities at 450 nm from bulk nasal spray solutions of metoclopramide hydrochloride

| Formulation No. | % Label Claim | Chromatographic Purity (% Peak Area) | % O.D. |
|---|---|---|---|
| 1 | 97.3 | 99.9 | 4.9 |
| 22 | 95.7 | 99.9 | 5.7 |
| 43 | 97.1 | 100.0 | 5.6 |
| 60 | 97.7 | 100.0 | 5.1 |
| Production | 96.5 | 100.0 | 5.2 |

The color and clarity stabilities under the storage conditions under normal conditions (25° C./60% RH) and accelerated conditions (40° C./75% RH) are presented as % optical densities in Tables 2-3a and 2-3b, respectively.

TABLE 2-3a

Color and clarity stabilities of five metoclopramide nasal spray solutions at 25° C./60% RH

| Formulation No. | T (0) | T (1 wk) | T (2 wk) | T (4 wk) | T (8 wk) |
|---|---|---|---|---|---|
| | | | % O.D. | | |
| F-1 | 4.9 | 8.8 | 11.1 | 12.7 | 6.4 |
| F-22 | 5.7 | 10.4 | 15.8 | 11.5 | 9.5 |
| F-43 | 5.6 | 10.1 | 13.9 | 10.4 | 8.9 |
| F-60 | 5.1 | 10.3 | 13.6 | 11.8 | 9.5 |
| F-P | 5.2 | 10.8 | 13.2 | 12.2 | 11.5 |
| | | | Absorbance | | |
| F-1 | 0.01196 | 0.02147 | 0.02708 | 0.03099 | 0.01562 |
| F-22 | 0.01391 | 0.02538 | 0.03855 | 0.02806 | 0.02318 |
| F-43 | 0.01366 | 0.02464 | 0.03392 | 0.02538 | 0.02172 |
| F-60 | 0.01244 | 0.02513 | 0.03318 | 0.02879 | 0.02318 |
| F-P | 0.01269 | 0.02635 | 0.03221 | 0.02977 | 0.02806 |

TABLE 2-3b

Color and clarity stabilities of five metoclopramide nasal spray solutions at 40° C./75% RH

| Formulation No. | T (0) | T (1 wk) | T (2 wk) | T (4 wk) | T (8 wk) |
|---|---|---|---|---|---|
| | | | % O.D. | | |
| F-1 | 4.9 | 12.0 | 14.9 | 16.9 | 22.3 |
| F-22 | 5.7 | 14.9 | 18.6 | 23.5 | 33.1 |
| F-43 | 5.6 | 13.1 | 15.0 | 17.3 | 21.9 |
| F-60 | 5.1 | 13.3 | 14.0 | 13.6 | 17.4 |
| F-P | 5.2 | 13.5 | 16.3 | 18.8 | 22.7 |
| F-1 | 0.01196 | 0.02928 | 0.03636 | 0.04124 | 0.05441 |
| F-22 | 0.01391 | 0.03636 | 0.04538 | 0.05734 | 0.08076 |
| F-43 | 0.01366 | 0.03196 | 0.0366 | 0.04221 | 0.05344 |
| F-60 | 0.01244 | 0.03245 | 0.03416 | 0.03318 | 0.04246 |
| F-P | 0.01269 | 0.03294 | 0.03977 | 0.04587 | 0.05539 |

No significant change in optical density was observed from each formulation under the storage conditions at 25° C./60% RH for 8 weeks. However, optical density increases were observed in all solutions tested at 40° C./75% RH for 8 weeks. Formulation F-22 demonstrated the most linear increase in optical density of all the formulations—about 2.5% per week between weeks 1 and 8.

Stability of pH

The pH of each formulation was also determined after 8 weeks at both storage conditions (25° C./60% RH and 40° C./75% RH) compared to their initial pH's, as shown in Table 2-4. All pH's at both storage conditions were within ±0.2 pH units of the starting pH's.

TABLE 2-4 pH stabilities of five metoclopramide nasal spray solutions after 8 wee storage at 25° C./60% RH and 40° C./75% RH

| Formulation No. | pH | | pH at T (8 wks) | |
|---|---|---|---|---|
| | Target pH | at T (0) | 25° C./60% RH | 40° C./75% RH |
| F-1 | 3.9 ± 0.2 | 3.80 | 3.76 | 3.67 |
| F-22 | 5.5 ± 0.2 | 5.20 | 5.43 | 5.30 |
| F-43 | 5.5 ± 0.2 | 5.52 | 5.48 | 5.37 |
| F-60 | 5.5 ± 0.2 | 5.40 | 5.26 | 5.24 |
| F-P | 5.5 ± 0.2 | 5.41 | 5.23 | 5.22 |

From the foregoing, it can be seen that formulation F-22 was the most greatly affected of all the tested samples.

Example 3

Stability Studies of Nasal Metoclopramide Compositions

Introduction and Background

An analytical testing method was developed to quantify discoloration of five metoclopramide hydrochloride nasal spray solutions employing guidelines in the United States Pharmacopeia (USP). See, 32 USP <631>, <1061> and <851>.

Preparation of Test Samples

A second set of samples (sample set #2) was prepared having the formulations set forth in Table 2-1, above, according to the procedure outlined in Example 2, except that the samples were exposed to ambient air by puncturing the stoppers of the containers with needles, which were left in place during testing.

The OD was measured at 450 nm on the first day (T(0)) and after 4 (T(4 wk)), and 8 (T(8 wk)) weeks, of storage under normal conditions (25° C./60% RH) and accelerated conditions (40° C./75% RH).

Five formulations (F-1, F-22, F-43, F-60 and F—P) containing about 200 mg/mL metoclopramide as free base were assayed for optical density. These data are presented in Table 3-1. Each freshly prepared formulation demonstrated a pale, light brownish color. The initial optical density of each formulation was determined to be about 5-6%, as calibrated with respect to a 0.0005 M iodine solution at 450 nm.

TABLE 3-1

Color and clarity stabilities of five metoclopramide nasal spray solutions at 40° C./75% RH

| Formulation No. | T (0) | T (4 wk) | T (8 wk) |
|---|---|---|---|
| F-1 | 6.1 | 11.9 | 15.7 |
| F-22 | 7.9 | 17.8 | 26.5 |
| F-43 | 7.6 | 10.9 | 13.0 |
| F-60 | 7.0 | 13.9 | 10.4 |
| F-P | 7.1 | 15.7 | 15.9 |

Optical density increases were observed in all solutions tested at 40° C./75% RH for 8 weeks. Formulation F-22 demonstrated the most linear increase in optical density of all the formulations.

A single formulation, prepared according to the description of F—P (200 mg/mL of metoclopramide free base) was stored, 7.5. mL per vial, in amber glass vials for from 0 to 6 months at the conditions indicated in the following Table 3-2. The color standard referenced in Table 3-2 is standard "E" per 32 USP <631>, as referenced hereinabove.

TABLE 3-2

Stability of Metoclopramide 200 mg/mL solution (F-P) at 1, 3 and 6 months.

| T0 | T-1 month 40° C./75% RH | T-3 months 25° C./60% RH | T-3 months 40° C./75% RH | T-6 months 25° C./60% RH | T-6 months 40° C./75% RH |
|---|---|---|---|---|---|
| Pale yellow solution | Pale yellow solution | Pale yellow solution | Pale yellow solution with color darker than standard solution | Pale yellow solution | Pale yellow solution with color darker than standard solution |

As can be seen in Table 3-2, under normal conditions (25° C./60% Relative Humidity), the solution was colorless to pale yellow (same or lighter than 32 USP <631>"E" color standard) up to 6 months. Additionally, under accelerated conditions (40° C./75% RH), the solution was colorless to pale yellow (same or lighter than 32 USP <631>"E" color standard) at one month, but darker than the standard solution at 3 and 6 months.

Example 4

Clinical Study of Nasally Administrable Metoclopramide Composition

Overall Study Design and Plan.

A multi-center, controlled, randomized, open-label, parallel design study in patients with diabetic gastroparesis is carried out. Eligible patients are randomized to receive metoclopramide nasal spray 10 mg, metoclopramide nasal spray 20 mg or oral metoclopramide 10 mg tablets in ratio 2:2:1 four times daily before meals and at bedtime for six weeks.

Treatments to be Administered

Intranasal Medication: The metoclopramide 200 mg/ml solution is packaged with a pump that delivers 0.05 ml per spray for the 10 mg strength or with a pump that delivers 0.1 ml per spray for the 20 mg strength. Patients randomized to receive metoclopramide nasal spray 10 mg or 20 mg received one spray per dose. The formulation is one of the formulations set forth in Example 1, above.

Randomized Treatment or Crossover Phase

Patients who are determined eligible for inclusion in the study following the screening visit are block-randomized within each center in a 2:2:1 ratio (metoclopramide nasal spray 10 mg, metoclopramide nasal spray 20 mg and oral metoclopramide 10 mg respectively) with a block size of 5.

Selection and Timing of Dose for Each Patient

All patients randomized to nasal spray are instructed to do the following: actuates the nasal spray device once into one nostril, four times daily, before meals and at bedtime; alternates nostrils with each application.

Patients randomized to oral metoclopramide tablets are instructed to take one tablet four times daily, 30 minutes before meals and at bedtime.

If the patient misses a meal, he/she is instructed to still take medication as scheduled. If the patient eats more than three meals in one day, he/she is instructed to not take additional medication. If a dose of medication is forgotten, he/she is advised to take it as soon as he/she remembers. Doses greater than 2 hours late are omitted. The patients are instructed not to take a double dose of the medication at the next scheduled time if a dose is missed.

Patients will begin taking the medication on study Day 1 and complete the study on Day 42.

Symptom Assessment

A symptom assessment tool, modified from the tool described by Perkel and colleagues (M. S. Perkel, T. Hersh, C. Moore, E. D. Davidson, "Metoclopramide Therapy in Fifty-five Patients With Delayed Gastric Emptying"; Am J Gastroenterol 1980; 74:231-236, which is incorporated herein in its entirety), is used to assess symptoms and therapeutic efficacy before, during, and at the conclusion of treatment. The modifications to the Perkel scale includes removal of items which are redundant or are not considered hallmark symptoms of gastroparesis. Simple language changes (medical to layman terminology) and more precise response specifications are also includes to increase inter-site consistency and are self-reported on the Symptom Assessment Questionnaire ("SAQ"). Patients are asked to rate the frequency of each of six target symptoms during the week prior to the assessment. The target symptoms are nausea, vomiting, anorexia, bloating, early satiety and meal tolerance. Patients assign each symptom a predefined ordinal frequency score of zero to four.

Also included is an assessment of severity in the evaluation of diabetic gastroparesis symptoms (W. S. Longo, A. M. Vernava; "Prokinetic Agents for Lower Gastrointestinal Motility Disorders", Dis Colon Rectum 1993; 36:696-708, incorporated by reference in its entirety). An Investigator's Assessment Questionnaire ("IAQ") is includes to assess the severity of the symptoms and therapeutic efficacy before, during, and at the conclusion of treatment following speaking to the patient.

A total symptom score is calculated as the sum of the ratings of the SAQ and IAQ.

Entry criteria for the study includes a total score of between 8 and 20 on each of the SAQ and IAQ, based upon a moderate or greater grading of at least two symptoms and varying grading on other symptoms. Patients with a score higher than 40 are excluded. On each of the scales (SAQ and IAQ), a minimum of two out of six symptoms must have been rated moderate (2) or higher.

Efficacy Parameters

Efficacy measurements include the patient's SAQ and IAQ scores. Both questionnaires are completed at baseline and once per week during the 6 week treatment period: Days 7, 14, 21, 28, 35 and 42, respectively.

The SAQ and IAQ each have 6 symptom items, including nausea, vomiting, loss of appetite, feeling bloated, feeling full after eating a small amount of food, and persistent fullness after eating. The SAQ assesses the frequency of the symptoms, whereas the IAQ examines the severity. The SAQ is completed first since the physician needs to discuss the symptoms with the patient prior to the completion of the IAQ.

Primary Efficacy Parameter

The primary efficacy endpoint is the change from the baseline to the end of the study in the total symptom score. The total symptom score is the sum of the six patient-rated frequency items plus the sum of the six investigator-rated severity items. If a patient terminates prematurely from the study, the last available total symptom assessment score is used.

Secondary Efficacy Parameter

The secondary efficacy endpoints involved both changes from baseline in the weekly total symptom scores and combined severity and frequency score (severity score plus frequency score) for each individual symptom. Each combined item has a possible score of 0 to 8.

Results

Efficacy Analysis

The primary efficacy endpoint for the study is the change in total symptom score between baseline and week 6. The primary analysis of efficacy is an intent-to-treat analysis where all patients who are randomized to one of the three treatments and have at least one post-randomization assessment (including SAQ and IAQ) are includes.

The secondary analysis of efficacy is a "per protocol" analysis which includes all patients who completed the study per protocol. This per protocol analysis is performed only for the primary efficacy endpoint, i.e., the change from baseline to the end of the study in the total symptom score. Patients who do not meet the baseline SAQ/IAQ score criteria are excluded. The SAQ and IAQ taken during the time interval in which prohibited concomitant therapies are taken are also excluded from the per protocol analysis.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pharmaceutical composition comprising metoclopramide, or a pharmaceutically-acceptable salt thereof, a citrate buffer, and benzalkonium chloride; wherein the composition is a nasal solution that is clear to pale yellow when compared to standard E, 32 USP <631> on storage at a temperature of 40° C. for at least about 4 weeks; and wherein the composition has a citrate concentration ([citrate]=[citric acid]+[dihydrogen citrate ion]+[hydrogen citrate ion]+[citrate ion]) of at least about 10 millimolar.

2. The pharmaceutical composition of claim 1, having a starting pH of at least about 4.5.

3. The pharmaceutical composition of claim 1, having a starting pH of at least about 5.0.

4. The pharmaceutical composition of claim 1, wherein the composition is substantially free of any additional antioxidant.

5. The pharmaceutical composition of claim 1, wherein the composition further comprises at least one member of the group consisting of a salt, EDTA, sorbitol, a sugar (including a reduced sugar, such as sorbitol) or a flavoring agent.

6. The pharmaceutical composition of claim 1, having a concentration of metoclopramide, or a pharmaceutically-acceptable salt thereof, of from about 20.0% (w/v) to about 30.0% (w/v).

7. The pharmaceutical composition of claim 1, having a concentration of benzalkonium chloride from about 0.005% (w/v) to about 0.05% (w/v).

8. The pharmaceutical composition of claim 1, having an osmolality of from about 500 mOsm/kg to about 1400 mOsm/kg.

9. The composition of claim 1, wherein the composition is a nasal solution that remains clear to pale yellow when compared to standard E, 32 USP <631> on storage at a temperature of about 40° C. for at least about 8 weeks.

10. A pharmaceutical composition comprising metoclopramide, or a pharmaceutically-acceptable salt thereof, a buffer, and benzalkonium chloride; wherein the composition is a nasal solution that is clear to pale yellow when compared to standard E, 32 USP <631> on storage at a temperature of 40° C. for at least about 4 weeks; and wherein the composition has a pH of above about 4.5.

11. The composition of claim 10, having a starting pH of at least about 4.6.

12. The composition of claim 10, wherein the composition remains clear to pale yellow when compared to standard E, 32 USP <631> on storage at a temperature of about 40° C. for at least about 8 weeks.

13. The composition of claim 10, wherein the buffer is selected from the group consisting of citric acid/phosphate, acetate, barbital, borate, Britton-Robinson, cacodylate, citrate, collidine, formate, maleate, McIlvaine, phosphate, Prideaux-Ward, succinate, citrate-phosphate-borate (Teorell-Stanhagen), veronal acetate, MES (2-(N-morpholino)ethanesulfonic acid), BIS-TRIS (bis(2-hydroxyethyl)iminotris(hydroxymethyl)methane), ADA (N-(2-acetamido)-2-iminodiacetic acid), ACES (N-(carbamoylmethyl)-2-aminoethanesulfonaic acid), PIPES (piperazine-N,N'-bis(2-ethanesulfonic acid)), MOPSO (3-(N-morpholino)-2-hydroxypropanesulfonic acid), BIS-TRIS PROPANE (1,3-bis(tris(hydroxymethyl)methylamino)propane), BES (N,N-bis(2-hydroxyethyl)-2-aminoethanesulfonaic acid), MOPS (3-(N-morpholino)propanesulfonic acid), TES (N-tris(hydroxymethyl)methyl-2-aminoethanesulfonic acid), HEPES (N-(2-hydroxyethyl)piperazine-N'-(2-ethanesulfonic acid), DIPSO (3-(N,N-bis(2-hydroxyethyl)amino)-2-hydroxypropanesulfonic acid), MOBS (4-(N-morpholino)butanesulfonic acid), TAPSO (3-(N-tris(hydroxymethyl)methylamino)-2-hydroxy-propanesulfonic acid), tris (hydroxymethylaminomethane, HEPPSO(N-(2-hydroxyethyl)piperazine-N'-(2-hydroxypropanesulfonic acid), POPSO (piperazine-N,N'-bis(2-hydroxypropanesulfonic acid)), TEA (triethanolamine), EPPS(N-(2-hydroxyethyl)piperazine-N'-(3-propane-sulfonic acid), TWINE (N-tris(hydroxymethyl)methylglycine), GLY-GLY (glycylglycine), BICINE (N,N-bis(2-hydroxyethyl)glycine), HEPBS (N-(2-hydroxyethyl)piperazine-N'-(4-butanesulfonic acid)), TAPS(N-tris(hydroxy-methypmethyl-3-aminopropanesulfonic acid), or AMPD (2-amino-2-methyl-1,3-propanediol) buffer.

14. A method of treating a patient, comprising intranasally administering to the patient an effective amount of a composition of claim 1.

15. The method of claim 14, wherein the patient has a disorder that is treatable with metoclopramide.

16. The method of claim 15, wherein said disorder that is treatable with metoclopramide is at least one member of the group consisting of gastroparesis, emesis, delayed emesis and nausea.

17. A pharmaceutical composition comprising metoclopramide, or a pharmaceutically-acceptable salt thereof, a citrate buffer, benzalkonium chloride, and less than about 1% w/v benzyl alcohol; wherein the composition is a nasal solution that is clear to pale yellow when compared to standard E, 32 USP <631> on storage at 40° C. for at least about 4 weeks; and wherein the composition has a citrate concentration ([citrate]=[citric acid]+[dihydrogen citrate ion]+[hydrogen citrate ion]+[citrate ion]) of at least about 10 millimolar.

18. The pharmaceutical composition of claim 17, wherein the concentration of benzyl alcohol is about 0.01 to about 0.8% w/v.

19. The pharmaceutical composition of claim 17, wherein said composition remains clear to pale yellow when compared to standard E, 32 USP <631> on storage at a temperature of about 40° C. for at least about 8 weeks.

20. The pharmaceutical composition of claim 17, having a starting pH of at least about 4.5.

21. The pharmaceutical composition of claim 20, having a starting pH of at least about 5.0.

22. The pharmaceutical composition of claim 17, wherein the composition is substantially free of any additional antioxidant.

23. The pharmaceutical composition of claim 17, wherein the composition further comprises at least one member of the group consisting of a salt, EDTA, sorbitol, a sugar (including a reduced sugar, such as sorbitol) or a flavoring agent.

24. The composition of claim 17, having a concentration of metoclopramide, or a pharmaceutically-acceptable salt thereof, of from about 20.0% (w/v) to about 30.0% (w/v).

25. The composition of claim 17, having a concentration of benzalkonium chloride from about 0.005% (w/v) to about 0.05% (w/v).

26. The composition of claim 17, having an osmolality of from about 500 mOsm/kg to about 1400 mOsm/kg.

27. A method of treating a patient, comprising intranasally administering to the patient an effective amount of a composition of claim 17.

28. The method of claim 27, wherein the patient has a disorder that is treatable with metoclopramide.

29. The method of claim 28, wherein said disorder that is treatable with metoclopramide is at least one member of the group consisting of gastroparesis, emesis, delayed emesis and nausea.

* * * * *